(12) United States Patent
Bandyopadhyay et al.

(10) Patent No.: US 9,302,967 B2
(45) Date of Patent: Apr. 5, 2016

(54) SUBSTITUTED CATHECHOLS AS INHIBITORS OF IL-4 AND IL-5 FOR THE TREATMENT OF BRONCHIAL ASTHMA

(75) Inventors: Santu Bandyopadhyay, Kolkata (IN); Balaram Ghosh, Kolkata (IN); Parasuraman Jaisankar, Kolkata (IN); Bikas Chandra Pal, Kolkata (IN); Siddhartha Roy, Kolkata (IN); Bholanath Paul, Lucknow (IN); Arjun Ram, New Delhi (IN); Ulaganathan Mabalirajan, New Delhi (IN); Nahid Ali, Kolkata (IN); Arun Bandopadhyay, Kolkata (IN); Aditya Konar, Kolkata (IN); Jayashree Bagchi Chakraborty, Kolkata (IN); Indrani Choudhury Mukherjee, Kolkata (IN); Jaydeep Chaudhuri, Kolkata (IN); Sanjit Kumar Mahato, Kolkata (IN); Anirban Manna, Kolkata (IN); Roma Sinha, Kolkata (IN); Pradyot Bhattacharya, Kolkata (IN); Jayaraman Vinayagam, Kolkata (IN); Deba Prasad Jana, Kolkata (IN); Sushovan Chowdhury, Kolkata (IN)

(73) Assignee: Council of Scientific & Industrial Research, Rafi Marg (IN)

( * ) Notice: Subject to any disclaimer, the term of this patent is extended or adjusted under 35 U.S.C. 154(b) by 55 days.

(21) Appl. No.: 14/110,869

(22) PCT Filed: Apr. 11, 2012

(86) PCT No.: PCT/IB2012/051757
§ 371 (c)(1),
(2), (4) Date: Jan. 27, 2014

(87) PCT Pub. No.: WO2012/140574
PCT Pub. Date: Oct. 18, 2012

(65) Prior Publication Data
US 2014/0135393 A1      May 15, 2014

(30) Foreign Application Priority Data

Apr. 11, 2011   (IN) .................. 01032/DEL/2011

(51) Int. Cl.
| A61K 31/14 | (2006.01) |
| A61K 31/05 | (2006.01) |
| C07C 39/19 | (2006.01) |
| A61K 31/15 | (2006.01) |
| A61K 31/215 | (2006.01) |
| A61K 31/277 | (2006.01) |
| A61K 31/36 | (2006.01) |
| C07C 69/017 | (2006.01) |
| C07C 69/732 | (2006.01) |
| C07C 251/40 | (2006.01) |
| C07C 251/66 | (2006.01) |
| C07C 255/36 | (2006.01) |
| C07D 317/50 | (2006.01) |

(52) U.S. Cl.
CPC ............... *C07C 39/19* (2013.01); *A61K 31/05* (2013.01); *A61K 31/15* (2013.01); *A61K 31/215* (2013.01); *A61K 31/277* (2013.01); *A61K 31/36* (2013.01); *C07C 69/017* (2013.01); *C07C 69/732* (2013.01); *C07C 251/40* (2013.01); *C07C 251/66* (2013.01); *C07C 255/36* (2013.01); *C07D 317/50* (2013.01)

(58) Field of Classification Search
None
See application file for complete search history.

(56) References Cited

U.S. PATENT DOCUMENTS

| 6,413,553 B1 * | 7/2002 | Bandyopadhyay et al. .. 424/734 |
| 2002/0086068 A1 | 7/2002 | Bandyopadhyay |

FOREIGN PATENT DOCUMENTS

| JP | 63 115834 A | 5/1988 |
| JP | 4 360855 A | 12/1992 |
| KR | 20000040361 A | * 7/2000 |

OTHER PUBLICATIONS

Ali et al. Annals of Clinical Microbiology and Antimicrobials 2010 (9) 1-9.*
KR20000040361A english abstract, Jul. 2000.*
International Search Report for PCT/IB2012/051757 dated Mar. 12, 2012.
Pandey, A., et al., "Modulation of Th1/Th2 cytokines and inflammatory mediators by hydroxychavicol in adjuvant induced arthritic tisues", Cytokine, Academic Press Ltd., Phila., PA US. vol. 49, No. 1. Jan. 1, 2010. pp. 114-121.

* cited by examiner

*Primary Examiner* — Jeffrey S. Lundgren
*Assistant Examiner* — Michael Schmitt
(74) *Attorney, Agent, or Firm* — Potter Anderson & Corroon LLP

(57) ABSTRACT

The present invention relates to compounds of general formula 1 for the treatment of bronchial asthma by inhibition of IL-4 or IL-5 pathway inhibition. The present invention also relates to the use of compound of general formula 1 for the treatment of bronchial by inhibition of IL-4 or IL-5 pathway. The present invention also relates to the method of treating asthma by inhibition of IL-4 or IL-5 pathway by administration of compound or said composition through oral, intranasal, route or by inhalation to a mammal in need thereof. Compound of general formula 1 may be used for reducing perivascular and peribronchial inflammation.

12 Claims, 14 Drawing Sheets

Comparative effect of Compound 1 of formula I with Dexa on AHR to Mch

Effect of Compound 1 of formula I on Lung IL-4 levels

Vehicle control    Compound 1 of formula I dose 47mg/kg

Scheme 1:

Scheme 2

Scheme 3:

SUBSTITUTED CATHECHOLS AS INHIBITORS OF IL-4 AND IL-5 FOR THE TREATMENT OF BRONCHIAL ASTHMA

This is a U.S. national filing, pursuant to 35 U.S.C. §371, of International Application No. PCT/IB2012/051757, filed Apr. 11, 2012, which claims benefit of Foreign Application No. 01032/DEL/2011, filed Apr. 11, 2011, the entire contents of each of which are incorporated by reference herein.

FIELD OF INVENTION

The present invention relates to pharmaceutical compositions including a compound of formula I or formula II (substituted catechols, as described herein below), for the treatment of bronchial asthma. These conditions may be treated by inhibition of IL-4 and IL-5.

BACKGROUND AND PRIOR ART DESCRIPTION

The incidence of asthma and respiratory allergy is increasing in epidemic proportion throughout the world. It is one of the most critical, torturous diseases, which is threatening human civilization. Current studies have shown that the loss due to asthma and other respiratory disorders is more that 30-34% of the total man-days. Even today there is no clear curative therapy for the disease. Moreover, currently available remedial drugs i.e., bronchodilators and steroids, are with undetermined responsiveness, and hazardous to health, with severe side effects.

The basic aspect of the disease is the blockage of air passage of the lungs, usually occurring due to the formation of leukotriene (LK) molecules from arachidonic acid (AA). LK acts on the cell surface receptor producing cellular oedema, swelling and mucus secretion. All these together cause constriction of air-passage resulting in the torturous and fatal disease-Asthma. The response to the three major classes of asthma therapy, beta-agonists, leukotriene antagonists, and inhaled corticosteroids, demonstrates wide inter-individual variability, with a significant number of non-responders.

Recent studies suggest that interleukin-4 (IL-4) mediates important proinflammatory functions in asthma including induction of IgE isotype switch and promotion of eosinophil transmigration across endothelium, mucous secretion and differentiation of T helper type 2 (Th2 type) lymphocytes. Therefore, IL-4 antagonists may have potential as therapeutic agent in asthma (Respiratory Research 2001, 2, 66-70).

The presence of increased numbers of airway eosinophils in asthmatic patients suggest that this cell plays a key role in the pathogenesis of asthma (Am. J. Respir. Crit. Care Med. 1999, 160, 1001-1008). Eosinophils produce proinflammatory mediators. IL-5 promotes eosinophil differentiation and activation, as well as trafficking into the lungs (Ann. Rev. Immunol. 2006, 24, 147-174). Thus, IL-5 antagonists may also have potential for the treatment of asthma.

Hydroxychavicol is known to induce cell cycle arrest and apoptosis in oral KB carcinoma cell line (Cell. Mol. Life Sci., 2004, 61, 83-96) and in hepatocarcinoma cells (Cancer lett., 2000, 155, 29-35). Hydroxychavicol has anti-oxidative property inducing cell-cycle arrest and apoptosis of oral KB carcinoma cells (British Journal of Pharmacology, 2002, 135, 619-630), anti-mutagenic property against tobacco-specific carcinogens (Mutat. Res., 1989, 210, 249 253), as well as chemopreventive activity against benzo[a]pyrene induced for stomach tumors in mice (J. Ethnopharmacol., 1991, 34, 207-213). Conflicting literature exists on the effect of hydroxychavicol on cycloxygenase 2: while one report suggested enhancement of expression (J. Oral Pathol. Med., 2003, 32, 522-529), another report suggested hydroxychavicol-mediated inhibition of platelet aggregation by suppression of cyclooxygenase, thromboxane production and calcium mobilization (British Journal of Pharmacology, 2007, 152, 73-82). Hydroxychavicol is a potent COX-1/COX-2 inhibitor and could be potentially used in prevention or treatment of cardiovascular disease through its anti-inflammatory effect (British Journal of Pharmacology, 2007, 152, 73-82). The chemopreventive efficacy of betel leaf extract and its constituents, including hydroxychavicol on 7,12-dimethylbenz(a)anthracene induced skin tumors in mouse, has been reported (Indian Journal of Experimental Biology, 1991, 29, 346-351). The anti-mutagenic and anti-carcinogenic properties of hydroxychavicol and eugenol have been reported (Mutagenesis, 1989, 4, 200-204). Another recent report suggested that allylpyrocatechol (hydroxychavicol) inhibited NF-κB pathway in lipopolysaccharide (LPS)-induced macrophages leading to suppression of iNOS, interleukin-12 and TNF-α (International Immunopharmacology, 2008, 8, 1264-1271).

The present invention relates to inhibition of IL-4 and IL-5 by hydroxychavicol (purified from natural sources or prepared synthetically) and its analogues and shows anti-asthmatic efficacy in vivo in mouse model.

OBJECT OF THE INVENTION

The main object of the present invention is to provide inhibitors of IL-4 and IL-5 Another object of the present invention is to provide the inhibitors for the treatment of bronchial asthma.

Another object of the present invention is to provide method of treatment of bronchial asthma.

Another object of the present invention is to provide usage of general formula 1 for the treatment of bronchial asthma by IL-4 and IL-5 inhibition pathway.

SUMMARY OF THE INVENTION

The present invention provides the use of one or more compounds of the general formulas:

i. a compound with general formula 1 having the structure:

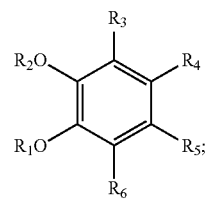

wherein $R_1$=—H or —COCH$_3$, $R_2$=—H or —COCH$_3$, or wherein $R_1$ and $R_2$ are covalently coupled to —CH$_2$— comprising a five member ring with the structure:

wherein $R_3$=—H;
wherein $R_4$=—H or —CH$_2$—CH=CH$_2$ or —CH$_2$—CH$_2$—CH$_3$ wherein $R_5$=—H or —$CH_2$—CH=$CH_2$; and
wherein $R_6$=—H or —$CH_2$—CH=$CH_2$;
ii. a compound with formula I having the structure:

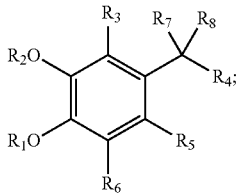

wherein $R_1$=—H or —$COCH_3$, $R_2$=—H or —$COCH_3$, or wherein $R_1$ and $R_2$ are covalently coupled to —$CH_2$— comprising a five member ring with the structure:

wherein $R_3$=—H;
wherein $R_4$=—CH=$CH_2$ or —$CH_2$—$CH_3$ or —CH=NOH or —CN or —CH=NOAc or —CH=CH—COOEt;
wherein $R_5$=—H or —$CH_2$—CH=$CH_2$;
wherein $R_6$=—H or —$CH_2$—CH=$CH_2$
wherein $R_7$=—H or —$CH_3$; and
wherein $R_8$=—H or —$CH_3$;
iii. a compound with formula II having the structure:

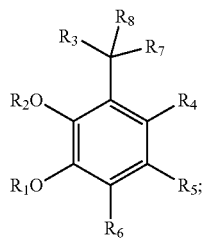

wherein $R_1$=—H or —$COCH_3$, $R_2$=—H or —$COCH_3$, or wherein $R_1$ and $R_2$ are covalently coupled to —$CH_2$— comprising a five member ring with the structure:

wherein $R_3$=—CH=$CH_2$
wherein $R_4$=—H or —$CH_2$—CH=$CH_2$ or —$CH_2$—$CH_2$—$CH_3$;
wherein $R_5$=—H or —$CH_2$—CH=$CH_2$;
wherein $R_6$=—H or —$CH_2$—CH=$CH_2$;
wherein $R_7$=—H; and
wherein $R_8$=—H; and
wherein one or more of said compounds are used for the treatment of Bronchial asthma.

In an embodiment of the present invention, the representative compounds are comprising of:

(1) 4-allyl-benzene-1,2-diol (hydroxychavicol),
(2) 4,5-diallylbenzene-1,2-diol,
(3) 3,4-diallylbenzene-1,2-diol,
(4) 4-allyl-5-propylbenzene-1,2-diol,
(5) 4,5-diallyl-1,2-phenylene diacetate,
(6) 3,4-diallyl-1,2-phenylene diacetate,
(7) 4-allyl-1,2-phenylene diacetate,
(8) 4-allyl-5-propyl-1,2-phenylene diacetate,
(9) 2-(3,4-dihydroxyphenyl)-2-methylpropanal oxime,
(10) 2-(3,4-dihydroxyphenyl)-2-methylpropanenitrile,
(11) 4-(2-cyanopropan-2-yl)-1,2-phenylene diacetate,
(12) 4-(1-(acetoxyimino)-2-methylpropan-2-yl)-1,2-phenylene diacetate,
(13) (E)-ethyl 4-(3,4-dihydroxyphenyl)-4-methylpent-2-enoate,
(14) 5-(2-methylbut-3-en-2-yl)benzo[d][1,3]dioxole,
(15) (E)-4-(5-ethoxy-2-methyl-5-oxopent-3-en-2-yl)-1,2-phenylene diacetate,
(16) 3-allyl-benzene-1,2-diol,
(17) 3-allyl-4-propylbenzene-1,2-diol,
(18) 3,4-diallyl-5-propylbenzene-1,2-diol,
(19) 3-allyl-1,2-phenylene diacetate,
(20) 3-allyl-4-propyl-1,2-phenylene diacetate and
(21) 3,4-diallyl-5-propyl-1,2-phenylene diacetate.

In yet another embodiment of the present invention, the bronchial asthma is treated by IL-4 or IL-5 pathway inhibition.

In still another embodiment of the present invention, the compound is administered through oral, intranasal, route or by inhalation to a mammal in need thereof.

In yet another embodiment of the present invention, compound of general formula 1 increase $PC_{200}$ Mch in the range of 0.1 mg to 10.0 mg per kg body weight.

In still another embodiment of the present invention, the concentration of the compound used for Inhibition of stimulation-induced IL-4 for $IC_{50}$ is in the range of 5 to 30 M.

In yet another embodiment of the present invention, the concentration of the compound used for Inhibition of stimulation-induced IL-5 for $IC_{50}$ is in the range of 4.5 to 35 M.

In still another embodiment of the present invention, the concentration of the compound used for reducing immunoglobulin E (IgE) is in the range of 0.1 mg to 10.0 mg per kg body weight.

In yet another embodiment of the present invention, the concentration of the compound used for reducing the lung inflammation is in the range of 5.0 mg to 10.0 mg per kg body weight.

In still another embodiment of the present invention, the compound is used for reducing perivascular and peribronchial inflammation.

In yet another embodiment of the present invention, the method of treatment of bronchial asthma in a patient suffering from bronchial asthma comprising administering to said patient an effective amount of a compound of general formula 1 by inhibiting IL-4 and IL-5.

In still another embodiment of the present invention, the compound of general formula 1 is administered orally.

In yet another embodiment of the present invention, the oral route is in the form of capsule, syrup, powder or granules.

In still another embodiment of the present invention, compound of general formula 1 is administered at a dosage level between (0.1 mg to 10.0 mg per kg body weight.) twice a day for 6 months.

To evaluate the effect of compound 1 of formula I on asthmatic features in mice, mice were sensitized, challenged and treated with VEH, compound of formula I and DEX as described in Examples. Dosage schedule was like this: one dose of compound of formula I/VEH was given 3 hrs before the OVA/PBS challenge & another dose was at 3 hrs after the challenge and for DEX, only one dose was given 3 hrs after the challenge. On day 28, 12-14 hrs after the $10^{th}$ challenge AHR to Methacholine was determined as described in the Examples. On day 30, 12-14 hrs after one more challenge (to synchronize the conditions between AHR measurement and sacrifice) mice were sacrificed for sampling.

Figure 2:
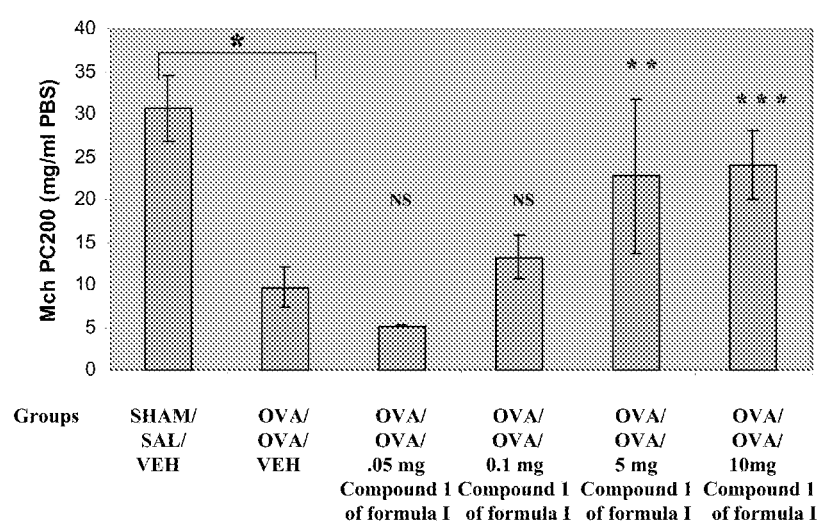

FIG. 2: Compound of formula I reduced AHR to Mch in a dose dependent manner:

To find out the effect of compound of formula I compound of formula I on the lung function, 12-14 hrs after OVA challenge AHR was measured as described in the Examples and the results were expressed as MCh PC200. compound of formula I has shown to be effective at higher concentrations. *P<0.001, NS (Nonsignificant),  P>0.05 and * P<0.01 versus OVA/OVA/VEH. Data are expressed as means±SDs (n=4 mice in each group).

Figure 3:
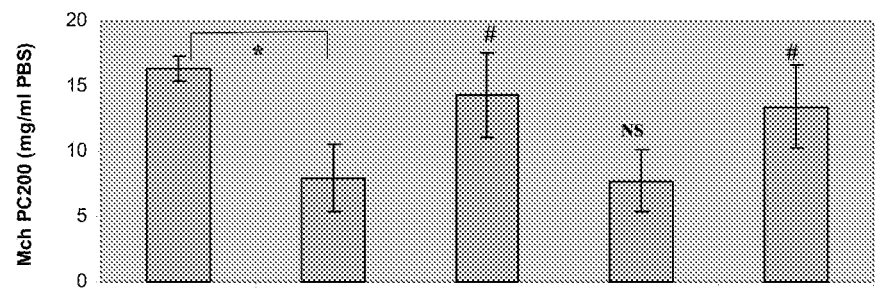

FIG. 3: Compound of formula I reduced AHR to Mch parallel to Dexamethasone (DEX):

To compare the effect of compound of formula I with the known anti-asthmatic compound, DEX, higher concentrations of compound of formula I were taken for further experiments. compound of formula I at 10 mg/kg significantly reduced the AHR to Mch as effective as DEX. *P<0.001 compared to OVA/OVA/VEH, NS (Nonsignificant), # P<0.05 compared to OVA/OVA/VEH. The results are expressed as means±SDs (n=5 mice in each group). Data shown here is the representative of two independent experiments.

Figure 4:
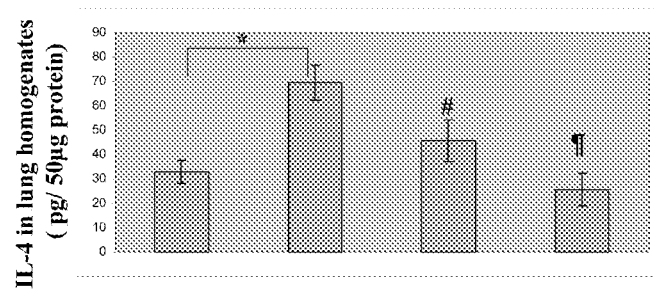

FIG. 4: Compound of formula I reduced IL-4 levels in lung:

To assess the effect of compound of formula I (10 mg) on the IL-4 levels in tissue, ELISA was done as described in the Examples and compared to DEX. OVA/OVA/VEH mice showed a significant increase in the levels of IL-4 in the lung. In contrast, mice group treated with 10 mg of compound of formula I (OVA/OVA/compound of formula I 10 mg) showed a significant reduction in the IL-4 levels. This reduction was approx. 65% compared to DEX treated mice. * P<0.01, # P=0.05 and ¶ P<0.05 (n=5 mice in each group).

Figure 5:
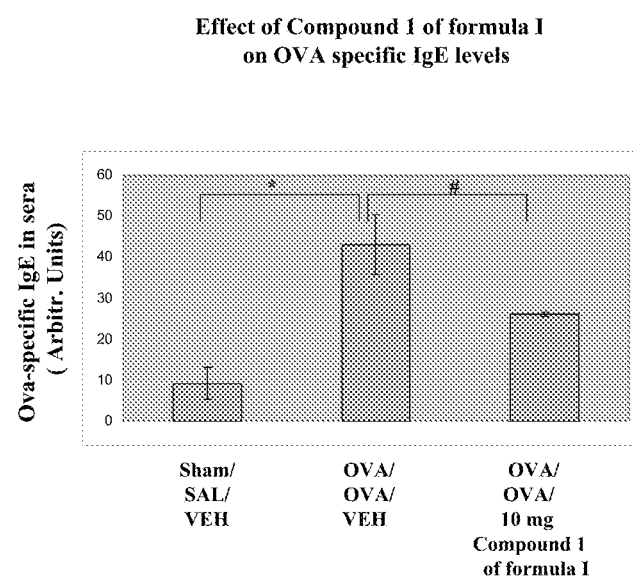

FIG. 5: Compound of formula I reduced OVA specific IgE levels in sera:

To assess the effect of compound of formula I 10 mg on OVA specific IgE levels in sera, ELISA was done as described in Examples. Results were expressed in arbitrary values after multiplying the OD at 450 with 100. OVA/OVA/VEH mice showed significant increased OVA specific IgE levels in sera and OVA/OVA/compound of formula I 10 mg mice showed significant reduction. * P<0.001, and # P<0.01 (n=5 mice each group).

Figure 6:
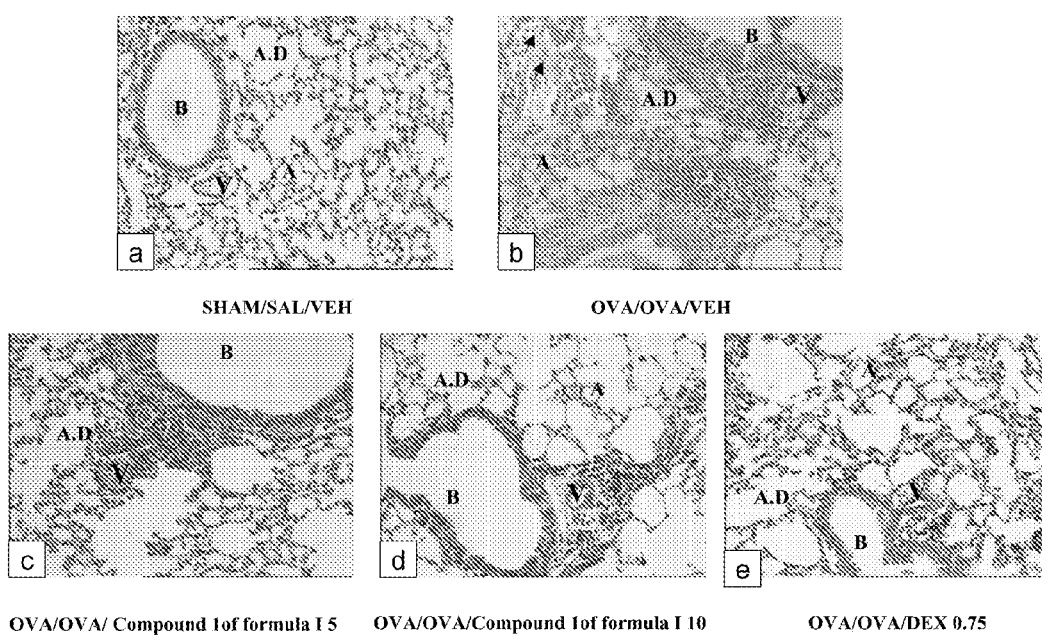

FIG. 6: Compound of formula I reduced lung inflammation:

To assess the effect of compound of formula I on lung inflammation, lung tissues were processed as described in the Examples. B=Bronchi. A.D=Alveolar duct, A=Alveoli, V=Vessel and black arrows in the inset showed the presence of the eosinophil both in the vascular wall and in the surrounding bronchi which indicate the eosinophil migration from vessel to bronchi. All the photomicrographs are shown at 10× magnification and inset in FIG. 6b is at 40×.

FIG. 7:

Spleen histology of mice after treatment with compound 1 of formula I (47 mg/kg).

FIG. 8:

Liver histology of mice after treatment with compound 1 of formula I (47 mg/kg).

FIG. 9:

Kidney histology of mice after treatment with compound 1 of formula I (47 mg/kg).

FIG. 10:

Lung histology of mice after treatment with compound 1 of formula I (47 mg/kg).

FIG. 11:

Heart histology of mice after treatment with compound 1 of formula I (47 mg/kg).

FIG. 12A-C:

Schematics showing synthesis of compounds of Formula I or II.

DETAILED DESCRIPTION OF THE INVENTION

The present invention provides for a compound of formula I or formula II or a pharmaceutical composition including a compound of formula I or formula II, that can be used for the treatment of malignancies.

An embodiment of the present invention relates to the use of substituted catechols that may be represented by Formula I (wherein $R_1$ to $R_8$ are as defined in Table 1) or Formula II (wherein $R_1$ to $R_8$ are as defined in Table 2).

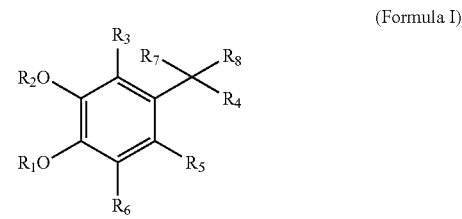

(Formula I)

TABLE 1

| Compound No | Substitutions | | | | | | | |
|---|---|---|---|---|---|---|---|---|
| | $R_1$ | $R_2$ | $R_3$ | $R_4$ | $R_5$ | $R_6$ | $R_7$ | $R_8$ |
| 1 | H | H | H | —CH=CH$_2$ | H | H | H | H |
| 2 | H | H | H | —CH=CH$_2$ | —CH$_2$—CH=CH$_2$ | H | H | H |
| 3 | H | H | H | —CH=CH$_2$ | H | —CH$_2$—CH=CH$_2$ | H | H |
| 4 | H | H | H | —CH$_2$—CH$_3$ | —CH$_2$—CH=CH$_2$ | H | H | H |
| 5 | —COCH$_3$ | —COCH$_3$ | H | —CH=CH$_2$ | —CH$_2$—CH=CH$_2$ | H | H | H |
| 6 | —COCH$_3$ | —COCH$_3$ | H | —CH=CH$_2$ | H | —CH$_2$—CH=CH$_2$ | H | H |
| 7 | —COCH$_3$ | —COCH$_3$ | H | —CH=CH$_2$ | H | H | H | H |
| 8 | —COCH$_3$ | —COCH$_3$ | H | —CH$_2$—CH$_3$ | —CH$_2$—CH=CH$_2$ | H | H | H |

TABLE 1-continued

| Compound No | R₁ | R₂ | R₃ | R₄ | R₅ | R₆ | R₇ | R₈ |
|---|---|---|---|---|---|---|---|---|
| 9 | H | H | H | —CH=NOH | H | H | —CH₃ | —CH₃ |
| 10 | H | H | H | —CN | H | H | —CH₃ | —CH₃ |
| 11 | —COCH₃ | —COCH₃ | H | —CN | H | H | —CH₃ | —CH₃ |
| 12 | —COCH₃ | —COCH₃ | H | —CH=NOAc | H | H | —CH₃ | —CH₃ |
| 13 | H | H | H | —CH=CH—COOEt | H | H | —CH₃ | —CH₃ |
| 14 | R₁, R₂ = —CH₂— | | H | —CH=CH₂ | H | H | —CH₃ | —CH₃ |
| 15 | —COCH₃ | —COCH₃ | H | —CH=CH—COOEt | H | H | —CH₃ | —CH₃ |

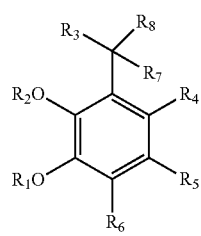

(Formula II)

TABLE 2

| Compound No | R₁ | R₂ | R₃ | R₄ | R₅ | R₆ | R₇ | R₈ |
|---|---|---|---|---|---|---|---|---|
| 16 | H | H | —CH=CH₂ | H | H | H | H | H |
| 17 | H | H | —CH=CH₂ | —CH₂—CH₂—CH₃ | H | H | H | H |
| 18 | H | H | —CH=CH₂ | —CH₂—CH=CH₂ | —CH₂—CH₂—CH₂ | H | H | H |
| 19 | —COCH₃ | —COCH₃ | —CH=CH₂ | H | H | H | H | H |
| 20 | —COCH₃ | —COCH₃ | —CH=CH₂ | —CH₂—CH₂—CH₃ | H | H | H | H |
| 21 | —COCH₃ | —COCH₃ | —CH=CH₂ | —CH₂—CH=CH₂ | —CH₂•CH₂•CH₂ | H | H | H |

Representative compounds of formula I or formula II, in accordance with the present invention include:
1) 4-allyl-benzene-1,2-diol (hydroxychavicol),
2) 4,5-diallylbenzene-1,2-diol,
3) 3,4-diallylbenzene-1,2-diol,
4) 4-allyl-5-propylbenzene-1,2-diol,
5) 4,5-diallyl-1,2-phenylene diacetate,
6) 3,4-diallyl-1,2-phenylene diacetate,
7) 4-allyl-1,2-phenylene diacetate,
8) 4-allyl-5-propyl-1,2-phenylene diacetate,
9) 2-(3,4-dihydroxyphenyl)-2-methylpropanal oxime,
10) 2-(3,4-dihydroxyphenyl)-2-methylpropanenitrile,
11) 4-(2-cyanopropan-2-yl)-1,2-phenylene diacetate,
12) 4-(1-(acetoxyimino)-2-methylpropan-2-yl)-1,2-phenylene diacetate,
13) (E)-ethyl 4-(3,4-dihydroxyphenyl)-4-methylpent-2-enoate,
14) 5-(2-methylbut-3-en-2-yl)benzo[d][1,3]dioxole,
15) (E)-4-(5-ethoxy-2-methyl-5-oxopent-3-en-2-yl)-1,2-phenylene diacetate,
16) 3-allyl-benzene-1,2-diol,
17) 3-allyl-4-propylbenzene-1,2-diol,
18) 3,4-diallyl-5-propylbenzene-1,2-diol,
19) 3-allyl-1,2-phenylene diacetate,
20) 3-allyl-4-propyl-1,2-phenylene diacetate and
21) 3,4-diallyl-5-propyl-1,2-phenylene diacetate.

Compound No. 1 (hydroxychavicol) was obtained from *Piper betle* extract as described in Example 2. Compound No. 1 (hydroxychavicol) can also be prepared synthetically and this is described in Example 3.

Synthesis of many of the compounds of formula I and formula II was accomplished starting with commercially available catechol. The process for the preparation of these compounds is disclosed in our copending patent application 0044DEL2009 filed on dated Dec. 1, 2009.

Synthesis of certain compounds of formula I and formula II was accomplished starting with commercially available 3,4-methylene-dioxy phenyl acetic acid. The synthesis is explained in Scheme 3:

A preferred embodiment of the present invention relates to the use of substituted catechols that may be represented by Formula I (wherein R₁ to R₈ are as defined in Table 3) or Formula II (wherein R₁ to R₈ are as defined in Table 4).

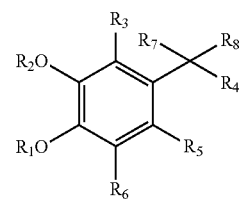

(Formula I)

TABLE 3

| Compound No | R₁ | R₂ | R₃ | R₄ | R₅ | R₆ | R₇ | R₈ |
|---|---|---|---|---|---|---|---|---|
| 1 | H | H | H | —CH=CH₂ | H | H | H | H |
| 7 | —COCH₃ | —COCH₃ | H | —CH=CH₂ | H | H | H | H |

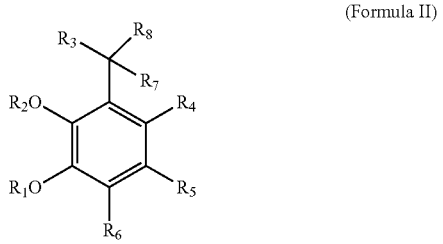

(Formula II)

TABLE 4

| Compound No | Substitutions | | | | | | | |
|---|---|---|---|---|---|---|---|---|
| | $R_1$ | $R_2$ | $R_3$ | $R_4$ | $R_5$ | $R_6$ | $R_7$ | $R_8$ |
| 16 | H | H | —CH=CH$_2$ | H | H | H | H | H |
| 19 | —COCH$_3$ | —COCH$_3$ | —CH=CH$_2$ | H | H | H | H | H |

Representative compounds of formula I or formula II, in accordance with the preferred embodiment of the present invention include:
4-allyl-benzene-1,2-diol (hydroxychavicol),
4-allyl-1,2-phenylene diacetate,
3-allyl-benzene-1,2-diol,
3-allyl-1,2-phenylene diacetate, The compounds of the present invention include the corresponding salts, isomers and polymorphs of the compounds of formula I and formula II.

The salts are pharmaceutically acceptable salts and are in particular salts which are non-toxic, or which can be used physiologically.

The term pharmaceutically acceptable salts is meant to include salts of the active compounds which are prepared with acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment.

Various polymorphs of compounds of the present invention can be prepared by crystallization of the compounds under different conditions. The different conditions are, for example, using different commonly used solvents or their mixtures for crystallization; crystallization at different temperatures; various modes of cooling, ranging from very fast to very slow cooling during crystallizations. Polymorphs can also be obtained by heating or melting the compound followed by gradual or fast cooling. The presence of polymorphs can be determined by IR (Infra-red) spectroscopy, solid probe NMR (Nuclear Magnetic Resonance) spectroscopy, differential scanning calorimetry, powder X-ray diffraction or such other techniques.

The present invention includes all possible geometric or cis-trans (E/Z) isomers of the compounds of the present invention. In the case of a cis/trans isomerism the invention includes both the cis form and the trans form as well as mixtures of these forms in all ratios. The preparation of individual isomers can be carried out, if desired, by separation of a mixture by customary methods.

The term "active ingredient" as used herein includes the compound of formula I or formula II.

The term "composition" includes formulations or other preparations that are suitable for administration to a mammal.

The term "treating", "treat" or "treatment" as used herein includes preventive (prophylactic) and palliative treatment.

As used herein, "safe and effective amount" means an amount of compound or composition, sufficient to significantly induce a positive modification in the condition to be regulated or treated, but low enough to avoid serious side effects (at a reasonable benefit/risk ratio), within the scope of sound medical judgment. The safe and effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable carrier utilized, and like factors. As used herein, all percentages are by weight unless otherwise specified.

As used herein, the term "mammal" includes a human.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician. In one aspect of the invention, the compound is administered in a daily dose of about 30 mg/kg of the body weight to about 300 mg/kg of the body weight, to a human in need thereof. The daily dose for a non-human mammal would be the same. The desired dose may conveniently be presented in a single dose or as divided doses administered at appropriate intervals, for example as two, three, four or more sub-doses per day.

The term "dosage form" refers to physically discrete units suitable as unit dosage forms for mammals such as humans. Each dosage form contains a predetermined quantity of active materials calculated to produce the desired therapeutic effect, in association with a suitable pharmaceutical carrier.

The compositions according to the invention may contain between 0.1-99% of the active ingredient, conveniently from 30-95% for tablets and capsules and 3-50% for liquid preparations.

As used herein, the term "pharmaceutically acceptable carrier" means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

In addition to the active ingredient and carrier substances, the pharmaceutical compositions may contain additives such as, for example, fillers, antioxidants, dispersants, emulsifiers, defoamers, flavors, preservatives, solubilizers or colorants.

In one aspect of the invention of the present invention, the additive may be selected from a group consisting of nutrients such as proteins, carbohydrates, sugars, talc, magnesium stearate, cellulose, calcium carbonate, starch-gelatin paste and/or pharmaceutically acceptable carriers, excipients, diluents or solvents.

In an aspect of the invention, the treatment methods and methods for reducing cellular proliferation described herein include the administration of pharmaceutical compositions described above, by known administration routes, modes, etc. including the following.

The composition can be administered orally, for example in the form of pills, tablets, coated tablets, capsules, granules, elixirs or syrup. The pharmaceutical composition may be in the forms normally employed, such as tablets, lozenges, capsules, powders, syrups, solutions, suspensions and the like specially formulated for oral, buccal, parenteral, transdermal, inhalation, intranasal, transmucosal, implant, or rectal administration. For buccal administration, the formulation may take the form of tablets or lozenges formulated in conventional manner. Tablets and capsules for oral administration may contain conventional excipients such as binding agents, (for example, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycolate) or wetting agents, such as sodium lauryl sulfate. The tablets may be coated according to methods well known in the art.

Alternatively, the compounds of the present invention may be incorporated into oral liquid preparations such as aqueous or oily suspensions, solutions, emulsions, syrups or elixirs. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle (e.g., sterile, pyrogen-free water) before use.

The following abbreviations/chemical formulae are employed in the Examples:

$Ac_2O$: acetic anhydride
$CH_2Cl_2$: dichloromethane
$CH_3I$: methyl iodide
DMAP: 4-(N,N-dimethyl)aminopyridine
DTT: dithiothreitol
EDTA: ethylene diamine tetra acetic acid
EGTA: ethylene glycol tetraacetic acid
$HCl.NH_2NHPh$: phenyl hydrazine hydrochloride
HCl: hydrochloric acid
HEPES: 4-(2-hydroxyethyl)-1-piperazineethanesulfonic acid
KCl: potassium chloride
$LiAlH_4$: lithium aluminium hydride
$MgCl_2$: magnesium chloride
NaCl: sodium chloride
$NaHCO_3$: sodium bicarbonate
NaOAc: sodium acetate
n-BuLi: n-Butyl Lithium
$NH_4Cl$: ammonium chloride
Pd: Palladium
t-BuOK: potassium t-butoxide Example 1

Collection of Plant Material

The leaves of *Piper betle* were collected from different areas of West Bengal, India. A voucher specimen was deposited at the Department of Medicinal Chemistry at the Indian Institute of Chemical Biology, Kolkata, India.

Example 2

Purification of Compound No. 1 from *Piper betle* Leaves

Compound No. 1: 4-Allyl-benzene-1,2-diol (hydroxychavicol)

Fresh leaves of *Piper betle* (5 kg) were collected, cut into small pieces, and homogenized with 4.0 liter of methanol in a blender. The homogenate was kept for 48 hours in a percolator and then it was passed through fine cheesecloth to filter out the large particles. The fine suspended particles in filtrate were removed by filtering through filter paper. The clear solution of methanol extract was evaporated to dryness under reduced pressure. All the solid particles were collected in the percolator and extraction was repeated with methanol two more times following the above method to get maximum yield. The combined methanol extract was dried to a semi-solid mass (106 g).

The methanol extract was partitioned between ethyl acetate and water. The aqueous layer was further extracted with n-butanol. Removal of the solvent in vacuo from ethyl acetate-soluble portion, n-butanol-soluble and aqueous phase yielded 46 g, 10.4 g and 50.1 g of fraction respectively. The ethyl acetate fraction (21 g) was subjected to silica gel chromatography with petroleum ether, chloroform-petroleum ether (1:1), chloroform-petroleum ether (9:1) and chloroform as eluants. Each eluant was evaporated to dryness and the residue was tested for bioactivity in various cancer cell-lines. The activity was found in the residue obtained from chloroform-petroleum ether (9:1) eluant (2.9 g). Rechromatography of this residue over silica gel using the same procedure furnished a pure compound (1.4 g) identified as hydroxychavicol (Compound No. 1), m.p. 48-49° C.

IR (Neat) cm$^{-1}$: 3360, 1607, 1519, 1441, 1281, 1110 and 913

$^1$H NMR (600 MHz, CDCl$_3$): δ 3.27 (d, 2H, J=7.2 Hz), 5.03-5.10 (m, 2H), 5.19 (brs, 2H), 5.89-5.95 (m, 1H), 6.63 (dd, J=1.8, 4.8 Hz, 1H), 6.71 (d, J=1.8 Hz, 1H), 6.79 (d, J=7.8 Hz, 1H).

$^{13}$C NMR (125 MHz, CDCl$_3$): δ 39.49, 115.32, 115.59, 115.67, 121.00, 133.24, 137.60, 141.64, 143.42.

MS (EI) m/z: 150 (M$^+$), 131, 123, 103, 77 and 51

The compound was characterized by comparison of the spectral data obtained with literature data available.

Melting points were recorded on a SPAC-N-SERVICE (India) open capillary melting point apparatus and are uncorrected.

NMR spectra were recorded on a Bruker DPX 300 MHz and Bruker DRX 600 MHz NMR instrument at room temperature and making a solution of samples in CDCl3 or DMSO-d6 solvent using tetramethylsilane (TMS) as the internal standard and are given in the δ (parts per million) scale. The peak shapes are denoted as follows: s, singlet; d, doublet; t, triplet; q, quartet; m, multiplet; dd, double doublet; br s, broad singlet.

Mass spectra, ESI and GCMS were recorded in a Micro mass Q-TOF Micro™ spectrometer and SHIMADZU GCMS-QP5050A GAS CHROMATOGRAPH MASS SPECROMETER using ZB-5 capillary column respectively. Mass spectral data, correspond to ESIMS or GCMS are given in m/z unit.

Infrared spectra were recorded on a JASCO-FT-IR Model-410. Spectra were calibrated against the polystyrene absorption at 1601 cm-1. Samples were scanned in neat or KBr discs. Analytical thin layer chromatography (TLC) was performed on standard Merck TLC silica gel 60 F254 aluminium sheets. Visualization of the spots on TLC plate was achieved either by exposure to iodine vapour or UV light. All reactions were monitored by employing TLC technique. Column chromatography was carried out on a silica gel 60-120 mesh.

All evaporation of solvents was carried out under reduced pressure on a EYELA Aspirator A-3S with EYELA Cool ACE-1111.

Example 3

Preparation of Compound No. 1 and Compound No. 16

Compound No. 1: 4-Allyl-benzene-1,2-diol

Compound No. 16: 3-Allyl-benzene-1,2-diol

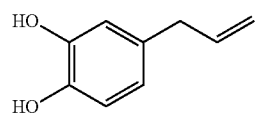

1

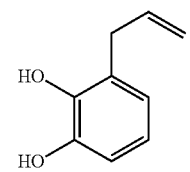

16

Step 1) Preparation of Compound B

Compound B: 2-(allyloxy)phenol

To a solution of pyrocatechol (Compound A) (5 g, 0.045 mol) in dry acetone (20 mL) was added dry potassium carbonate (K$_2$CO$_3$) (6.36 g, 0.044 mol) in portions for 30 minutes. The reaction mixture was stirred at room temperature for 1 hour. Allyl bromide (3.84 mL, 0.045 mol) was then added to the above mixture over 30 minutes. The reaction mixture was refluxed at 60-70° C. for 5 hours. After completion of the reaction, K$_2$CO$_3$ was filtered off. The filtrate was concentrated and extracted with chloroform (3×75 mL), washed with brine (1×50 mL) and dried over anhydrous sodium sulfate. The crude material was purified by column chromatography over silica gel (silica gel; 60-120 mesh) using increasing concentration of chloroform in petroleum ether. Eluants of 4% chloroform in petroleum ether, on concentration, yielded pure Compound B as a thick orange coloured liquid.

Yield: 5.8 g (85%), $^1$H NMR (300 MHz, CDCl$_3$): δ 4.59 (d, J=4.29 Hz, 2H) 5.35 (qt, J=17.2, 10.46 Hz, 2H), 5.69 (s, 1H), 6.04-6.08 (m, 1H) 6.81-6.96 (m, 4H).

Mass (ESI) m/z: 149 [M-H]$^-$

Step 2) Preparation of Compound No. 1 and Compound No. 16

The compound B (5 g, 0.033 mol) was heated at 170° C. temperature for 2 hours under N$_2$ atmosphere. After completion of the reaction, the crude reaction mixture was purified by column chromatography (silica gel: 60-120) using petroleum ether with increasing concentration of chloroform. The pure compounds corresponding to Compound No. 16 and Compound No. 1 were eluted with 45% and 75% chloroform in petroleum ether respectively.

Compound No. 1:
Yield: 900 mg (18%); White solid
M. P.: 40-45° C.,
$^1$H NMR (600 MHz, CDCl$_3$): δ 3.27 (d, 2H, J=7.2 Hz), 5.03-5.10 (m, 2H), 5.19 (brs, 2H), 5.89-5.95 (m, 1H), 6.63 (dd, J=1.8, 4.8 Hz, 1H), 6.71 (d, J=1.8 Hz, 1H), 6.79 (d, J=7.8 Hz, 1H).
$^{13}$C NMR (125 MHz, CDCl$_3$): δ 39.49, 115.32, 115.59, 115.67, 121.00, 133.24, 137.60, 141.64, 143.42.
GCMS m/z: 150 [M$^+$, 100%]

Compound No. 16:
Yield: 2.7 g (54%); Colourless liquid
$^1$H NMR (600 MHz, CDCl$_3$): δ 3.42 (d, J=6 Hz, 2H), 5.15-5.20 (m, 2H), 5.31 (s, 1H, —OH), 5.45 (s, 1H, —OH), 5.99-6.1 (m, 1H), 6.67-6.78 (m, 3H).
$^{13}$C NMR (125 MHz, CDCl$_3$): δ 35.04, 113.61, 116.50, 120.74, 121.98, 125.88, 136.45, 141.98, and 143.96.
GCMS m/z: 150 [M$^+$, 100%]

Example 4

Preparation of Compound No. 4 and Compound No. 17

Compound No. 4: 4-allyl-5-propylbenzene-1,2-diol

Compound No. 17: 3-allyl-4-propylbenzene-1,2-diol

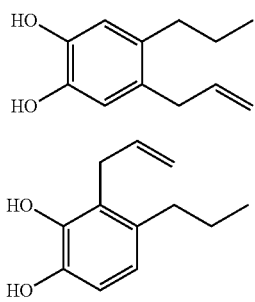

Step 1) Preparation of Compound C

Compound C: 4-propylbenzene-1,2-diol

To a solution of Compound No. 1 (5 g, 0.033 mol) as obtained in Example 3, in dry methanol (30 mL) was added 10% Pd-charcoal (750 mg, 1.5 eq.). The reaction mixture was stirred at room temperature for 2 hours. After complete disappearance of the starting material, the reaction mixture was filtered over a bed of Celite using methanol. The filtrate was concentrated and purified by column chromatography (silica gel: 60-120 mesh) using petroleum ether with increasing proportion of chloroform. The eluant of 60% chloroform in petroleum ether, on concentration, gave the desired compound C.

Yield: 4.8 g (95%); Colourless liquid
$^1$H NMR (300 MHz, CDCl$_3$): δ 0.98 (t, J=7.31 Hz, 3H), 1.58-1.72 (m, 2H), 2.58 (t, J=7.64 Hz, 2H), 5.05 (brs, 2H), 6.60 (d, J=6.62 Hz, 1H), 6.67 (d, J=6.69 Hz, 1H), 6.75 (s, 1H).
GCMS m/z: 152 [M$^+$, 100%]

Step 2) Preparation of Compound No. 4 and Compound No. 17

Compound C (1 g, 0.0066 mol) and dry acetone (15 mL) were stirred for 30 minutes and then dry K$_2$CO$_3$ (0.832 g, 0.0059 mol) was added in portions for 30 minutes. The stirring was continued for another hour. Allyl bromide (0.499 mL, 0.0058 mol) was then added to the mixture for 30 minutes. The reaction mixture was refluxed for 5 hours. After completion of the reaction, the reaction mixture was filtered. The filtrate was concentrated and extracted with chloroform (3×50 mL), washed with brine (1×50 mL) and dried over anhydrous sodium sulfate. The solvent was then removed under reduced pressure. The crude material was heated at 175-180° C. for 2 hours. After complete disappearance of the starting material, the reaction mixture was purified by column chromatography (silica gel: 60-120 mesh) using petroleum ether with increasing concentration of chloroform. The pure compounds corresponding to Compound No. 17 and Compound No. 4 were eluted at 25% and 45% chloroform in petroleum ether respectively.

Compound No. 4:
Yield: 200 mg (15%); colourless liquid
$^1$H NMR (300 MHz, CDCl$_3$): δ 0.97 (t, J=7.24 Hz, 3H), 1.57-1.67 (m, 2H), 2.54 (t, J=7.82 Hz, 2H), 3.39 (d, J=6.18 Hz, 2H), 4.9-5.39 (m, 4H), 5.9-6.07 (m, 1H), 6.60 (s, 1H), 6.65 (s, Hz, 1H).
Mass (ESI) m/z: 191[M-H]$^-$ Compound No. 17:
Yield: 260 mg (20.58%); light yellow liquid.
$^1$H NMR (300 MHz, CDCl$_3$): δ 0.97 (t, J=7.22 Hz, 3H), 1.59-1.67 (m, 2H), 2.57 (t, J=7.54 Hz, 2H), 3.31 (d, J=5.94 Hz, 2H), 5.01 (d, J=8.0, 2H), 5.35 (s, 1H), 5.59 (s, 1H), 5.88-5.9 (m, 1H), 6.59 (d, J=7.54 Hz, 1H), 6.66 (d, J=7.54 Hz, 1H).
Mass (ESI) m/z: 191[M-H]$^-$ Example 5

Preparation of Compound No. 18

Compound No. 18:
3,4-diallyl-5-propylbenzene-1,2-diol

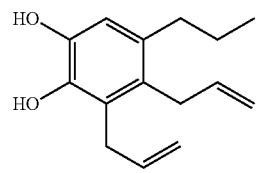

Compound No. 4 (0.100 g, 0.00052 mol) as obtained in Example 4, and dry acetone (5 mL) were stirred for 30 minutes and then dry K$_2$CO$_3$ (0.065 g, 0.000468 mol) was added in portions for 30 minutes. The stirring was continued for another hour. Allyl bromide (0.04 mL, 0.000468 mol) was added to the mixture over a period of 30 minutes. Then the reaction mixture was refluxed for 5 hours. After completion of the reaction, the reaction mixture was filtered. The filtrate was concentrated, extracted with chloroform (3×10 mL), washed with brine (1×10 mL) and dried over anhydrous sodium sulfate. The solvent was removed under reduced pressure. The crude material was heated at 175-180°C for 2 hours. The reaction mixture was cooled to room temperature and purified by column chromatography (silica gel: 60-120 mesh) using petroleum ether with increasing proportion of chloroform. The eluant of 25% chloroform in petroleum ether, on concentration, afforded pure compound corresponding to Compound No. 18 as a colourless liquid.

Yield: 27 mg (22.4%); colourless liquid.

$^1$H NMR (300 MHz, CDCl$_3$): δ 0.94 (t, J=7.29 Hz, 3H), 1.45-1.56 (m, 2H), 2.51 (t, J=7.98 Hz, 2H), 3.26 (d, J=7.1, 2H) 3.29 (d, J=7.3, 2H), 5.01-5.31 (m, 6H), 5.90 6.1 (m, 2H), 6.51 (s, 1H).

Mass (ESI) m/z: 231 [M-H]$^-$

Example 6

Preparation of Compound No. 2 and Compound No. 3

Compound No. 2: 4,5-diallylbenzene-1,2-diol

Compound No. 3: 3,4-diallylbenzene-1,2-diol

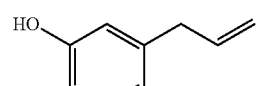

2

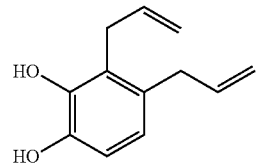

3

To a solution of pyrocatechol (Compound A) (1 g, 0.009 mol) and dry acetone (10 mL) was added dry K$_2$CO$_3$ (2.646 g, 0.0189 mol) in portions for 30 minutes. The stirring was continued for another hour. Allyl bromide (1.6 mL, 0.0189 mol) was added to the mixture for 30 minutes and the mixture was refluxed for 5 hours. After completion of the reaction, the solid was filtered and filtrate was concentrated and extracted with chloroform (3×50 mL), washed with brine (1×50 mL), dried over anhydrous sodium sulfate and solvent was removed under reduced pressure. The crude material was heated at 175-180° C. for 2 hours. The reaction mixture was purified by column chromatography (silica gel: 60-120 mesh) using petroleum ether with increasing concentration of chloroform. Elution of 60% and 75% chloroform in petroleum ether yielded pure compounds corresponding to Compound No. 2 and Compound No. 3 as liquids respectively.

Compound No. 2

Yield: 220 mg (12.86%); light yellow liquid $^1$H NMR (300 MHz, CDCl$_3$): δ 3.21 (d, 4H, J=6.21 Hz), 5.01-5.08 (m, 4H), 5.15 (brs, 2H), 5.81-5.92 (m, 2H), 6.76 (s, 2H).

$^{13}$C NMR (75 Hz, CDCl$_3$): δ 35.28 (2C), 116.64 (2C), 121.83 (2C), 124.48 (2C), 137.06 (2C), 142.66 (2C).

Mass (ESI) m/z: 189 [M-H]$^-$

Compound No. 3

Yield: 140 mg (8.18%); brown liquid.

$^1$H NMR (300 MHz, CDCl$_3$): δ 3.30 (d, 2H, J=6.13 Hz), 3.42 (d, J=5.82 Hz, 2H), 4.98-5.12 (m, 6H), 5.91-5.99 (m, 2H), 6.64 (s, 1H), 6.73 (s, 1H).

Mass (ESI) m/z: 189 [M-H]$^-$

Example 7

Preparation of Compound Nos. 5, 6, 7, 8, 19, 20, 21

Compound No. 5: 4,5-diallyl-1,2-phenylene diacetate

Compound No. 6: 3,4-diallyl-1,2-phenylene diacetate

Compound No. 7: 4-allyl-1,2-phenylene diacetate

Compound No. 8: 4-allyl-5-propyl-1,2-phenylene diacetate

Compound No. 19: 3-allyl-1,2-phenylene diacetate

Compound No. 20: 3-allyl-4-propyl-1,2-phenylene diacetate

Compound No. 21: 3,4-diallyl-5-propyl-1,2-phenylene diacetate

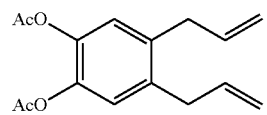

5

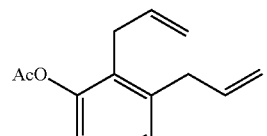

6

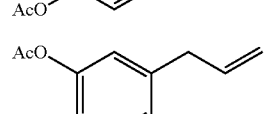

7

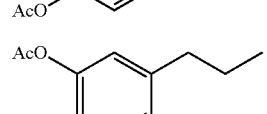

8

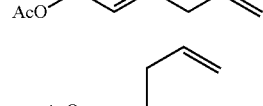

19

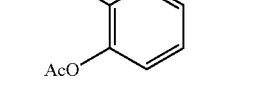

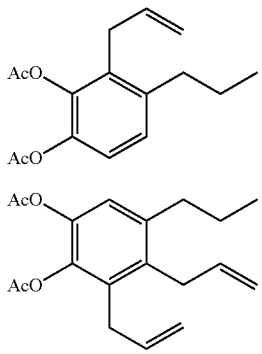

Representative Method:

To a solution of Compound No. 16 (1 g, 0.0066 mol) as obtained in Example 3, in dry pyridine (4 mL) was added acetyl chloride (1.05 mL, 0.0146 mol) under ice-cold conditions for 30 minutes. The reaction mixture was heated at 60-70° C. for 4 hours. After completion of the reaction, the solvent was removed under reduced pressure using rotary evaporator to leave a solid mass. The crude product was purified by column chromatography over silica gel (60-120 mesh) using petroleum ether with increasing proportion of chloroform. Eluant of 20% chloroform in petroleum ether yielded Compound No. 19 as white powder. This was further crystallized from chloroform in petroleum ether.

Spectral data of compounds corresponding to Compound No. 7 and Compound No. 19 are given below as representative data:

Compound No. 7:

Yield: 0.86 g (55%), colourless liquid.

$^1$H NMR (300 MHz, CDCl$_3$): δ 2.18 (s, 3H), 2.24 (s, 3H), 3.36 (d, J=6.6 Hz, 2H), 5.09 (d, J=13.4, 2H), 5.85-5.97 (m, 1H), 6.99 (s, 1H), 7.10 (d, J=14 Hz, 2H).

$^{13}$C NMR (75 MHz, CDCl$_3$): δ 20.32 (2C), 39.18, 116.37, 122.92, 123.14, 126.39, 136.20, 138.65, 140.08, 141.69, 168.03, 168.12.

GCMS m/z: 234 (M$^+$, 100%)

Compound No. 19:

Yield: 0.7 g (45%), white powder m.p.: 58-60° C.

$^1$H NMR (300 MHz, CDCl$_3$): δ 2.27 (s, 3H), 2.29 (s, 3H), 3.34 (d, J=6.49 Hz, 2H), 5.08 (d, J=12.45 Hz, 2H), 5.80-5.95 (m, 1H), 7.05-7.24 (m, 3H).

$^{13}$C NMR (75 MHz, CDCl$_3$): δ 20.29, 20.62, 34.51, 116.56, 121.39, 126.28, 127.42, 134.01, 135.31, 140.61, 142.51, 167.99, and 168.29.

GCMS m/z: 234 [M]$^+$

Example 8

Preparation of Compound No. 9

Compound No. 9:
2-(3,4-dihydroxyphenyl)-2-methylpropanal oxime

Step 1) Preparation of Methyl 1,3-benzodioxol-5-yl acetate (Compound E)

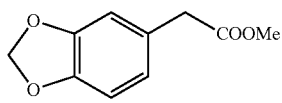

A solution of commercially available 3,4-(methylenedioxy)-phenyl acetic acid (Compound D) (5.00 g, 27.75 mmol) in methanol (20 mL) was cooled at 0° C. and thionyl chloride (2.5 mL, 28.85 mmol) added drop wise and the reaction mixture was stirred for 30 minutes. The reaction mixture was evaporated to dryness, diluted with ethyl acetate and washed with saturated, aqueous NaHCO$_3$ and water respectively. The organic layer was dried over anhydrous sodium sulfate, filtered and then concentrated. Purification on silica gel using 6:1 petroleum ether-ethyl acetate as eluant afforded Compound E (5.00 g, 93%) as a colourless oil.

$^1$H NMR (600 MHz, CDCl$_3$): δ 6.78-6.70 (m, 3H, aromatic protons), 5.94 (s, 2H, OCH$_2$O), 3.69 (s, 3H, CO$_2$CH$_3$), 3.54 (s, 2H, CH$_2$CO$_2$CH$_3$).

Step 2) Preparation of Methyl 2-(1,3-benzodioxol-5-yl) propanoate (Compound F)

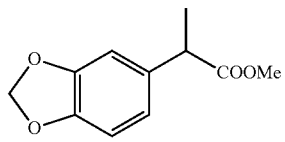

To a solution of diisopropylamine (3.46 mL, 24.78 mmol) in tetrahydrofuran (15 mL) at 0° C., n-BuLi (1.6 M in hexane) (15.45 mL, 24.66 mmol) was added dropwise under N$_2$ atmosphere. The solution was stirred at 0° C. for 30 minutes and then cooled to −78° C. A solution of Compound E (4.00 g, 20.59 mmol) in tetrahydrofuran (15 mL) was then added dropwise. The reaction mixture was stirred at −78° C. for 2 hours and then CH$_3$I (6.4 mL, 102.99 mmol) was added dropwise. The resulting mixture was stirred overnight at −78° C. The reaction was quenched with saturated, aqueous NH$_4$Cl solution and was allowed to attain room temperature. The solution was diluted with diethyl ether and washed with distilled water. The organic layer was dried over anhydrous sodium sulfate, filtered and concentrated. Purification on silica gel column using 12:1 petroleum ether-ethyl acetate as eluant yielded Compound F (4.00 g, 77.6%) as a light yellow oil.

$^1$H NMR (600 MHz, CDCl$_3$): δ 6.81-6.74 (m, 3H, aromatic protons), 5.94 (s, 2H, OCH$_2$O), 3.66 (s, 3H, CO$_2$CH$_3$), 3.64 (q, 1H, CHCH$_3$, J=7.2 Hz), 1.46 (d, 3H, CH$_3$, J=7.2 Hz)

Step 3) Preparation of Methyl 2-(1,3-benzodioxol-5-yl)-2-methyl propanoate (Compound G)

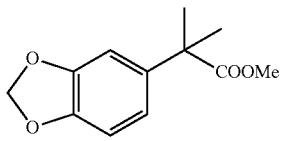

Compound F (4.26 g, 20.46 mmol) was treated with LDA (lithium diisopropylamide) and CH$_3$I in dry tetrahydrofuran under the similar condition as described for the preparation of compound 6 to obtain Compound G. After purification on silica gel column using 12:1 petroleum ether-ethyl acetate as eluant afforded the desired compound G (4.34 g, 95%) as a yellow oil.

¹H NMR (600 MHz, (CDCl₃): δ 6.84-6.75 (m, 3H, aromatic protons), 5.94 (s, 2H, OCH₂O), 3.65 (s, 3H, CO₂CH₃), 1.55, 1.54 (2s, 6H, 2CH₃).

Step 4) Preparation of 2-(1,3-benzodioxol-5-yl)-2-methyl propan-1-ol (Compound H)

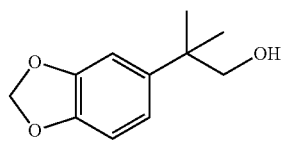

The solution of Compound G (3.94 g, 17.73 mmol) in dry tetrahydrofuran (15 mL) was added dropwise to an ice cooled (0° C.) suspension of LiAlH₄ (740 mg, 19.50 mmol) in dry tetrahydrofuran (15 mL). After completion of addition, the reaction mixture was stirred at 0° C. for 30 minutes and then at room temperature for additional 2 hours. It was then cooled to 0° C. and a saturated aqueous solution of sodium sulfate added dropwise. The reaction mixture was further stirred for 30 minutes to destroy excess LiAlH₄, filtered, washed with diethyl ether and obtained Compound H as a white solid (3 g, 87%).

¹H NMR (300 MHz, CDCl₃): δ 6.89-6.76 (m, 3H, aromatic protons), 5.94 (s, 2H, OCH₂O), 3.56 (s, 2H, CH₂OH), 1.29 (s, 6H, 2CH₃).

Step 5) Preparation of 2-(1,3-benzodioxol-5-yl)-2-methyl propanal (Compound I)

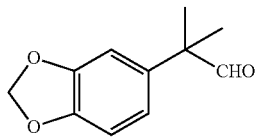

A suspension of 3 A° molecular sieves (6.5 g) in CH₂Cl₂ (15 mL) was stirred at room temperature for 30 minutes and then PCC (pyridinium chlorochromate) (2 g) was added. To this PCC suspension, a solution of Compound H (1 g, 5.15 mmol) in dry CH₂Cl₂ (15 mL) was added dropwise and was stirred at room temperature for 3.5 hours. The reaction mixture was evaporated to dryness and purified by silica gel column. Elution with diethyl ether afforded desired Compound I (700 mg, 71%) as a light yellow oil.

¹H NMR (300 MHz, CDCl₃): δ 9.43 (s, 1H, CHO), 6.82-6.72 (m, 3H, aromatic protons), 5.96 (s, 2H, OCH₂O), 1.56 (s, 6H, 2CH₃).

Step 6) Preparation of 2-(1,3-benzodioxol-5-yl)-2-methyl propanal oxime (Compound J)

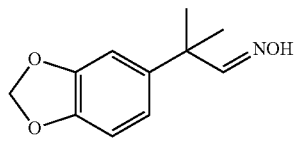

To a solution of Compound I (511 mg, 2.66 mmol) in ethanol (1 mL), HCl.NH₂OH (277 mg, 4.00 mmol) and pyridine (2.2 mL, 26.58 mmol) were added and it was stirred at room temperature for 1.5 hours. The reaction mixture was evaporated to dryness and added 10 mL of ethyl acetate. The organic layer was washed with distilled water, dried over anhydrous sodium sulfate, filtered and evaporated. The crude reaction mixture was purified over silica gel column using 5:1 petroleum ether-ethyl acetate as solvent to afford Compound J (528 mg, 96%) as a white foam.

¹H NMR (300 MHz, CDCl₃): δ 7.44 (s, 1H, CH=NOH), 6.82-6.77 (m, 3H, aromatic protons), 5.94 (s, 2H, OCH₂O), 1.45 (s, 6H, 2CH₃).

Step 7) Preparation of Compound No. 9

Compound No. 9: 2-(3,4-dihydroxyphenyl)-2-methylpropanal oxime

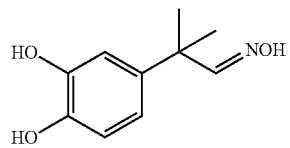

To a suspension of anhydrous AlCl₃ (193 mg, 1.45 mmol) in dry CH₂Cl₂ (1 mL), a solution of Compound J (60 mg, 0.29 mmol) in dry CH₂Cl₂ (1 mL) was added drop-wise at room temperature under N₂ atmosphere and stirred at the same temperature for 3 hours. The reaction mixture was cooled to 0° C., 20 mL of cold distilled water was added, the reaction mixture was allowed to attain room temperature and stirred for 12 hours at the same temperature under N₂ atmosphere. The reaction mixture was evaporated to dryness and triturated several times with 2:1 ethyl acetate-CH₂Cl₂ and followed by 10:1 ethyl acetate-methanol. The organic solutions were combined and evaporated to dryness. The crude material was purified by preparative thin-layer chromatography using 2:1 petroleum ether-ethyl acetate to obtain the desired Compound No. 9 (30 mg, 53%) as a white foam.

¹H NMR (300 MHz, CD₃OD): δ 7.36 (s, 1H, CH=NOH), 6.77-6.62 (m, 3H, aromatic protons), 1.40 (s, 6H, 2CH₃). ¹³C NMR (75 MHz)

¹³C NMR (75 MHz, CD₃OD): δ 158.75 (CH=NOH), 146.11, 144.75, 139.26, 118.23, 116.20, 114.60 (aromatic carbons), 41.09 [>C(CH₃)₂], 27.32 [>C(CH₃)₂].

Mass spectrum (EI, m/z): 195 (M)⁺(C₁₀H₁₃NO₃ requires 195.2).

Example 9

Preparation of Compound No. 12

Compound No. 12: 4-(1-(acetoxyimino)-2-methyl-propan-2-yl)-1,2-phenylene diacetate

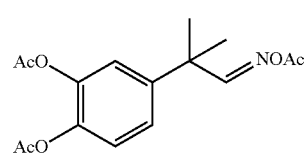

A mixture of Compound No. 9 (5 mg, 0.03 mmol), Ac₂O (36 μL, 0.39 mmol), catalytic amount of DMAP and pyridine (200 μL) was kept at room temperature for 48 hours. The reaction mixture was quenched with 20 μL of cold distilled water, evaporated to dryness and co-evaporated three times 3×200 μL with toluene. The crude reaction mixture was purified over silica gel column using 5:1 petroleum ether-ethyl acetate as solvent to afford Compound No. 12 (5 mg, 52%) as an oil.

$^1$H NMR (300 MHz, CDCl$_3$): δ 7.67 (s, 1H, CH=NOH), 7.26-7.12 (m, 3H, aromatic protons), 2.31, 2.30, 2.29 (3s, 9H, OCOCH$_3$), 1.57 (s, 6H, 2CH$_3$).

$^{13}$C NMR (75 MHz, CDCl$_3$): δ 168.72, 168.29, 168.25 (3OCOCH$_3$), 163.65 (CH=NOAc), 142.97, 142.07, 140.98, 124.51, 123.56, 121.44 (aromatic carbons), 41.53 [>C(CH$_3$)$_2$], 25.99 [>C(CH$_3$)$_2$], 20.66, 20.61 and 19.59 (3OCOCH$_3$).

Mass spectrum (ESI, m/z): 344.2 (M+Na)$^+$(C$_{16}$H$_{19}$NO$_6$Na requires 344.2).

Example 10

Preparation of Compound No. 10

Compound No. 10: 2-(3,4-dihydroxyphenyl)-2-methylpropanenitrile

Step 1) Preparation of 1-(2-(benzo[d][1,3]dioxol-5-yl)-2-methylpropylidene)-2-phenylhydrazine (Compound L)

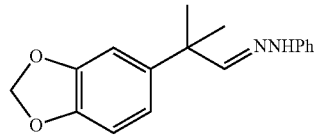

L

To a solution of Compound I (100 mg, 0.52 mmol) in ethanol (1 mL), HCl.NH$_2$NHPh (90 mg, 0.62 mmol) and NaOAc (85 mg, 1.04 mmol) were added and it was stirred at room temperature for 30 minutes. The reaction mixture was evaporated to dryness and 5 mL of CH$_2$Cl$_2$ added. The organic layer was washed with distilled water, dried over anhydrous sodium sulfate, filtered and evaporated. The crude reaction mixture having more than 95% of hydrazone corresponding to Compound L was used directly in next step, as it was unstable on silica gel. Hydrazone corresponding to Compound L was also confirmed from the mass spectra of the crude mixture.

Step 2) Preparation of Compound No. 10

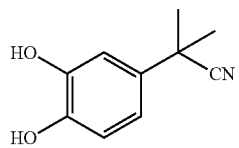

10

On removal of methylenedioxy group of Compound L (50 mg, 0.18 mmol) under similar conditions as described in the preparation of Compound No. 9, the expected dihydroxy hydrazone derivative was not observed. Purification by preparative thin-layer chromatography using 2:1 petroleum ether-ethyl acetate afforded the rearranged cyano compound corresponding to Compound No. 10 (20 mg, 58%) as a reddish oil.

$^1$H NMR (300 MHz, CD$_3$OD): δ 6.92-6.76 (m, 3H, aromatic protons), 1.65 (s, 6H, 2CH$_3$).

$^{13}$C NMR (75 MHz, CD$_3$OD): δ 146.77, 146.14, 134.55, 126.31, 117.42, 116.58, 113.66 (aromatic carbons and —C≡N), 37.80 [>C(CH$_3$)$_2$], 29.71 [>C(CH$_3$)$_2$]

IR (neat) V$_{max}$: 2242.

Mass spectrum (EI), m/z: 177 (M)$^+$(C$_{10}$H$_{11}$NO$_2$ requires 177.2).

Example 11

Preparation of Compound No. 13

Compound No. 13: (E)-ethyl 4-(3,4-dihydroxyphenyl)-4-methylpent-2-enoate

Step 1) Preparation of Ethyl 4-(1,3-benzodioxol-5-yl)-4-methyl pent-2-enoate (Compound K)

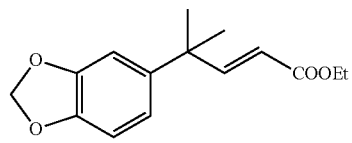

K

To a suspension of 60% NaH (11.2 mg, 0.28 mmol) in dry tetrahydrofuran (0.4 mL) at 0° C., triethyl phosphonoacetate (TEPA) (60 mL, 0.26 mmol) was added. The mixture was allowed to attain room temperature, stirred at the same temperature for 1 hour and again cooled to 0° C. To this mixture at 0° C., a solution of Compound I (30 mg, 0.16 mmol) in dry CH$_2$Cl$_2$ (0.8 mL) was added drop-wise and stirred at room temperature overnight. The reaction mixture was poured into distilled water (1 mL) and extracted with diethyl ether. The ether layer was dried over anhydrous sodium sulfate, filtered and evaporated. Purification on silica gel column using 20:1 petroleum ether-ethyl acetate afforded Compound K (30 mg, 72%) as a colourless oil.

$^1$H NMR (300 MHz) (CDCl$_3$): δ 7.07 (d, 1H, J 15.8 Hz, =CHCOOEt), 6.79-6.75 (m, 3H, aromatic protons), 5.93 (s, 2H, CH$_2$O), 5.78 (d, 1H, J 15.8 Hz, >CH=CHCOOEt), 4.19 (q, 2H, CO$_2$CH$_2$CH$_3$), 1.42 [s, 6H, >C(CH$_3$)$_2$], 1.29 (t, 3H, CO$_2$CH$_2$CH$_3$).

Step 2) Preparation of Compound No. 13

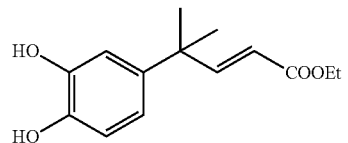

13

Removal of methylenedioxy group of Compound K (154 mg, 0.587 mmol) was performed under similar conditions as described in the preparation of Compound No. 9. Purification by preparative thin-layer chromatography using 5:1 petroleum ether-ethyl acetate afforded the desired Compound No. 13 (72 mg, 50%) as a reddish oil.

$^1$H NMR (300 MHz, CDCl$_3$): δ 7.08 (d, 1H, J=15.8 Hz, =CHCOOEt), 6.80-6.68 (m, 3H, aromatic protons), 5.78 (d, 1H, J=15.8 Hz, >CH═CHCOOEt), 5.55 (s, 2H, 2 phenolic-OH), 4.20 (q, 2H, CO$_2$CH$_2$CH$_3$), 1.40 [s, 6H, >C(CH$_3$)$_2$], 1.30 (t, 3H, CO$_2$CH$_2$CH$_3$).

$^{13}$C NMR (75 MHz) (CDCl$_3$): δ 168.21 (CO$_2$Et), 158.36 (CH═CHCO$_2$Et), 143.67, 142.23, 139.05 (aromatic carbons), 118.18, 117.25, 115.10, 113.53 (aromatic carbons, CH═CHCO$_2$Et), 60.77 (CO$_2$CH$_2$CH$_3$), 40.38 [>C(CH$_3$)$_2$], 27.71 [>C(CH$_3$)$_2$], 14.10 (CO$_2$CH$_2$CH$_3$).

Mass spectrum (EI, m/z): 250 (M)$^+$(C$_{14}$H$_{18}$O$_4$ requires 250.3).

Example 12

Preparation of Compound No. 14

Compound No. 14:
5-(2-methylbut-3-en-2-yl)benzo[d][1,3]dioxole

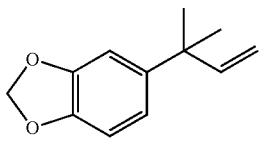

14

A suspension of methyl triphenyl phosphonium bromide (325 mg, 0.95 mmol) and t-BuOK (87.5 mg, 0.78 mmol) in dry tetrahydrofuran (1 mL) was stirred at 0° C. for 1 hour. To this mixture at 0° C., a solution of Compound I (50 mg, 0.26 mmol) in dry tetrahydrofuran (1 mL) was added dropwise. The reaction mixture was stirred at 0° C. for 1 hour and at room temperature for 2 hours and then refluxed for 5 hours. It was then cooled to 0° C. and quenched by NH$_4$Cl solution with stirring for 30 minutes. The reaction mixture was then extracted with diethyl ether. The ether layer was washed with distilled water, dried over anhydrous sodium sulfate, filtered and evaporated. Purification on silica gel column using petroleum ether followed by with 20:1 petroleum ether-ethyl acetate afforded desired Compound No. 14 (1 mg) as colourless oil.

$^1$H NMR (300 MHz, CDCl$_3$): δ 6.85-6.72 (m, 3H, aromatic protons), 6.02-5.91 (m, 3H, >CH═CH$_2$, OCH$_2$O), 5.06-5.00 (m, 2H, >CH═CH$_2$), 1.36 [s, 6H, >C(CH$_3$)$_2$].

Example 13

Preparation of Compound No. 11 and Compound No. 15

Compound No. 11:
4-(2-cyanopropan-2-yl)-1,2-phenylene diacetate

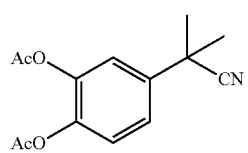

11

Compound No. 15: (E)-4-(5-ethoxy-2-methyl-5-oxopent-3-en-2-yl)-1,2-phenylene diacetate

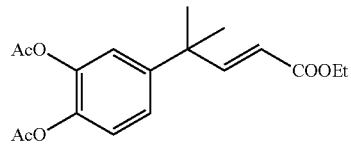

15

Representative Method:

A mixture of Compound No. 13 (25 mg, 0.10 mmol) as obtained in Example 11, Ac$_2$O (0.2 mL, 2.0 mmol), catalytic amount of DMAP and pyridine (0.2 mL) was kept at room temperature for 48 hours. The reaction mixture was quenched with 0.2 mL of cold distilled water, evaporated to dryness and co-evaporated three times 3×0.2 mL with toluene. The crude reaction mixture was purified over silica gel column using 5:1 petroleum ether-ethyl acetate as solvent to afford Compound No. 15 (23 mg, 76%) as an oil.

$^1$H NMR (300 MHz, CDCl$_3$): δ 7.26-7.06 (m, 4H, aromatic protons, ═CHCOOEt), 5.83 (d, 1H, J=14.0 Hz, >CH═CHCOOEt), 4.20 (q, 2H, CO$_2$CH$_2$CH$_3$), 2.29, 2.28 (2s, 6H, CH$_3$CO), 1.45 [s, 6H, >C(CH$_3$)$_2$], 1.29 (t, 3H, CO$_2$CH$_2$CH$_3$).

$^{13}$C NMR (75 MHz) (CDCl$_3$): δ 168.21, 168.23, 166.85 (2COCH$_3$, CO$_2$Et), 156.07 (CH═CHCO$_2$Et), 145.39, 141.74, 140.41, 124.48, 123.13, 121.24, 118.50 (aromatic carbons, CH═CHCO$_2$Et), 60.41 (CO$_2$CH$_2$CH$_3$), 40.76 [>C(CH$_3$)$_2$], 27.81 [>C(CH$_3$)$_2$], 20.65, 20.61 (2COCH$_3$), 14.22 (CO$_2$CH$_2$CH$_3$).

Mass spectrum (EI, m/z): 334 (M)$^+$(C$_{18}$H$_{22}$O$_6$ requires 334.37).

Example 14

Effects of Compounds of Formula I and II on IL-4 and IL-5

Normal human peripheral blood mononuclear cells (PBMC) were stimulated with phytohemagglutinin (PHA) 10 μg/ml in the presence and absence of varying concentrations of compounds of formula I and II. Culture supernatants were harvested and IIL-4 and IL-5 cytokines were quantitated by Cytometric Bead Array (CBA™) kit (Becton Dickinson, USA) following manufacturers instructions using a Flow Cytometer (BD LSR, Becton Dickinson) and CBA™ analysis software (Becton Dickinson). Results are given in Table 1.

TABLE 1

Inhibition of stumulation-induced IL-4 and IL-5 by compounds of formula I and II*
IC50 inhibitory activity (micro molar)

| Compound No | IL-4 | IL-5 |
|---|---|---|
| 1** | 5.0 | 4.5 |
| 1 | 5.0 | 5.0 |
| 7 | 4.0 | 4.0 |
| 16 | 30.0 | 30.0 |
| 19 | 30.0 | 35.0 |

Data are mean of triplicate cultures and represent one of three similar experiments.
**Isolated from *Piper betle* leaves

Example 15

Measurement of Bronchial Hyperresponsiveness, Serum IgE, Lung IL-4 and Lung Inflammation in Mouse Model of Experimental Asthma Mice Acclimatization:

BALB/c mice (6-8 wks old, 18-22 grams) were obtained from IICB Kolkata and VPCI, Delhi. Ethical clearance has been obtained from Institutional Ethical Committee. Mice were acclimatized for at least one week under the laboratory conditions (25±2° C., 60% humidity) before starting the experiments. After one week, baseline Penh (enhanced pause) was measured in Buxco unrestrained single chamber plethysmography (WBP, Buxco, Troy, N.Y.). The mice showed high fluctuations in baseline Penh were excluded from the study.

Figure 1:
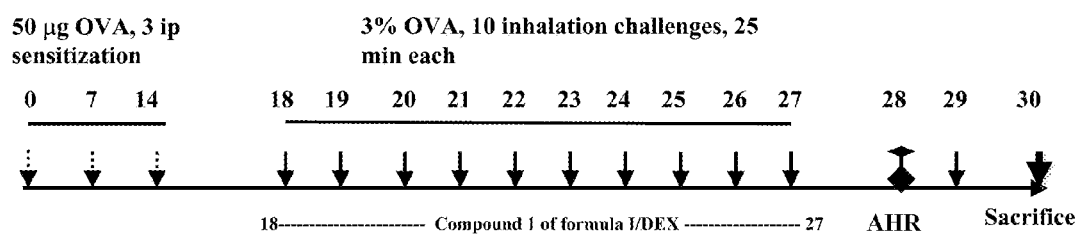
FIG. 1: Experimental protocol.

Sensitization and Challenge:

Mice were sensitized with 0.2 ml PBS containing 50 µg ovalbumin (OVA) (Sigma, USA) and 4 mg aluminum hydroxide in saline intraperitonially (i.p.) on days 0, 7 and 14 as shown in FIG. 1. Sham group mice were sensitized with only alum dissolved in PBS. From day 18 to 27, mice were exposed to aerosol of OVA (3%) inhalation 25 minutes daily in a Plexiglas chamber ($20\times20\times10$ cm$^3$). The aerosol was generated by a nebulizer (OMRON CX model) with an airflow rate of 9 L/minute. Sham group mice were challenged with PBS alone.

Oral Treatment of Mice with Compound 1 of Formula I:

Randomly mice were divided into 7 groups, 3-4 mice in each group as shown in FIG. 2. Compound 1 of formula I was dissolved in 50% ethanol. So 50% ethanol was used as a vehicle. Group I was alum sensitized, saline challenged and treated with vehicle (SHAM/SAL/VEH), group II was OVA sensitized, OVA challenged and treated with 50% ethanol as vehicle (OVA/OVA/VEH), group III, IV, V, VI were OVA sensitized, OVA challenged and treated with 0.05, 0.1, 5 and 10 mg/kg compound 1 of formula I. Drug was given in the volume of 10 µl orally twice per day. Confirmatory experiments were done with two concentrations of compound 1 of formula I (5 and 10 mg/kg twice a day), and these findings were compared with parallel group of mice which were OVA-sensitized, -OVA challenged and treated orally once a day with 0.75 mg/kg Dexamethasone (OVA/OVA/DEX).

Determination of Airway Responsiveness:

Airway responsiveness was measured by barometric plethysmography using whole-body plethysmography (WBP; Buxco, Troy, N.Y.) 12 hours after last saline or ovalbumin challenge. At the time of measurement the animals were awake and breathing spontaneously. Enhanced pause (Penh) to methacholine as measured using barometric plethysmography is a valid indicator of bronchoconstriction in mice and can be used to measure AHR (Am J Respir Crit Care Med 1997, 156, 766-775). Baseline Penh was taken initially, and then PBS followed by increasing concentrations (4-48 mg/ml) of methacholine was nebulized through an inlet of the main chamber for 3 min. Readings were taken and averaged for 5 minutes from the starting time of nebulisation. Airway responsiveness to MCh was evaluated by the concentration of MCh required to increase the Penh to twice the baseline value (MCh PC$_{200}$).

Measurement of IL-4 and OVA-Specific IgE:

OVA-specific IgE levels in sera were measured by enzyme linked immunosorbent assay (ELISA) as described previously with little modification (Inflam. Res. 2003, 52, 101-106). Absorbance values at 450 nm were converted to arbitrary values by multiplying with 100. IL-4 levels in lung homogenates were measured by ELISA method as per manufacturer's instructions (BD Pharmingen, USA). Lung homogenates were prepared by homogenizing the lung tissue (approximately 100 mg) with 1 ml PBS followed by centrifugation at 10000 g for 30 min at 4° C. Results were expressed in pg/50 µg protein. Protein estimation was done by BCA method.

Histological Analysis of Lung Inflammation:

The excised lung portion was fixed in 10% buffered formalin. The fixed, paraffin embedded tissue were cut into 4 µm sections and stained with haematoxylin-eosin (H&E) to assess inflammation.

Results:

Compound 1 of Formula I Reduced the Airway Hyperreactivity to Methacholine

As shown in FIG. 2, OVA/OVA/VEH mice showed decreased (about 3 fold) Mch PC$_{200}$ value compared to SHAM/SAL/VEH mice. This indicates that the mice were properly sensitized and challenged which caused airway hyperresponsiveness. Interestingly, when the sensitized and challenged mice were treated with compound 1 of formula I at increasing concentrations (0.05, 0.1, 5 and 10 mg/kg body weight), the PC$_{20}$) Mch values were found to be increased in a dose dependent manner (FIGS. 2 and 3). The maximum improvement was found with 10 mg compound 1 of formula I/kg dose. To compare the efficacy of compound 1 of formula I with dexamethasone, a standard drug, mice were divided into 5 groups: SHAM/SAL/VEH, OVA/OVA/VEH, OVA/OVA/DEX, OVA/OVA/compound 1 of formula I 5 mg, OVA/OVA/compound 1 of formula I 10 mg. Dexamethasone (0.75 mg/kg) was administered orally once per day. As shown in FIG. 3, it was observed that compound 1 of formula I (10 mg/kg) was able to improve lung function almost similar to the level of dexamethasone.

Compound 1 of Formula I Reduced the IL-4 and OVA Specific IgE:

OVA/OVA/VEH mice showed a significant increase in IL-4 levels in lung homogenates and OVA specific IgE levels in sera (P<0.01) compared to SHAM/SAL/VEH mice. Interestingly, the mice group treated with 10 mg of compound 1 of formula I (OVA/OVA/compound 1 of formula I 10 mg) has shown a decrease in the IL-4 levels (P=0.05 vs. OVA/OVA/VEH). Similarly it also significantly reduced the OVA specific IgE levels in sera (P<0.01 vs. OVA/OVA/VEH).

Compound 1 of Formula I Reduced the Lung Inflammation:

The extent of the lung inflammation in the mice lungs were assessed by H & E staining of the paraffin embedded sections. Representative photomicrographs are shown in FIG. 6. The lungs of SHAM/SAL/VEH mice showed normal structure with no sign of inflammation (FIG. 6*a*). The lungs of OVA/OVA/VEH mice showed a significant increase in the perivascular and peribronchial distribution of inflammatory cells (FIG. 6*b*, inset showed migration of eosinophils from the vessel to bronchi). Noticeably, the OVA-sensitized and OVA-challenged mice treated with 5 mg of compound 1 of formula I (OVA/OVA/compound 1 of formula I 5 mg) showed mild reduction of inflammation (FIG. 6c), whereas the OVA-sensitized and OVA-challenged mice group treated with 10 mg of compound 1 of formula I (OVA/OVA/compound 1 of formula I 10 mg) showed a significant reduction in both peribronchial and perivascular inflammation (FIG. 6d). This reduction of inflammation was almost comparable with mice treated with 0.75 mg Dexamethasone (FIG. 6e).

Example 16

14 d Acute Oral Toxicity of Compound 1 of Formula I 14 d acute oral toxicity of compound 1 of formula I was performed. Three doses were selected: 47, 23, 12 and 0 mg/kg bw (Vehicle control) of compound 1 of formula I was administered by single oral gavage using blunt ended steel canula.

On the day of administering the drug transient symptoms of restlessness and rapid rate of respiration that persisted for 30 minutes post administration were observed. Feed and water consumption in compound 1 of formula I treated mice and rats were comparable to vehicle control group.

Single oral administration of compound 1 of formula I at the dose of 47 mg/kg bw; 23 mg/kg bw and 12 mg/kg bw did not result in any morbidity and/or mortality. Gross physical examinations did not reveal any signs of diagnostic clinical importance. There was no noticeable behavioral change in any of the treated groups of mice.

TABLE 2

Changes in body weight of mice treated with compound of formula I

| Compound 1 of formula I (mg/kg bw) | day 0 | day 14 |
|---|---|---|
| 47 | 36.76 ± 2.33 | 36.45 ± 3.51 |
| 23 | 36.88 ± 4.87 | 36.26 ± 4.04 |
| 12 | 38.01 ± 5.77 | 37.38 ± 3.93 |
| Vehicle control | 33.36 ± 3.13 | 34.2 ± 4.2 |

No significant changes in the body weight of mice and rat treated with compound 1 of formula I was observed with respect to sham treated control (Table 2).

Hematology:

Before sacrifice, blood was drawn from the retro-orbital sinus of mice and rats with the help of non-heparinised capillary tubes and hematological parameters were assessed with the help of Automatic Hematology Analyzer (Medonic). Detailed hematology is presented in Table 3. No significant changes in the RBC, WBC, platelet counts, hemoglobin concentration and other related parameters were observed.

TABLE 3

Hematological tests with relevant base line values

| Parameters | Vehicle control | 47 mg/kg bw | 23 mg/kg bw | 12 mg/kg bw |
|---|---|---|---|---|
| RBC ($\times 10^6$/mm$^3$) | 8.69 ± 0.509 | 9.74 ± 0.749 | 10.05 ± 1.477 | 9.52 ± 1.313 |
| MCV ($\mu m^3$) | 40.05 ± 1.626 | 40.45 ± 1.126 | 41.675 ± 2.069 | 41.76 ± 1.268 |
| HCT (%) | 34.85 ± 3.46 | 39.12 ± 1.76 | 42.05 ± 7.86 | 39.72 ± 5.27 |
| PLT ($10^3$/mm$^3$) | 562 ± 223 | 476.5 ± 124 | 518 ± 40 | 588 ± 198 |
| MPV ($\mu m^3$) | 7.1 ± 0.28 | 7.1 ± 0.32 | 6.95 ± 0.36 | 6.96 ± 0.33 |
| WBC ($\times 10^3$/mm$^3$) | 10.6 ± 5.23 | 11.02 ± 2.61 | 13.52 ± 2.71 | 9.1 ± 0.86 |
| HGB (g/dL) | 11.35 ± 1.62 | 13.2 ± 0.65 | 13.22 ± 1.72 | 12.6 ± 2.50 |
| LYMF(%) | 1.05 ± 0.63 | 1.0 ± 0.87 | 2.12 ± 3.45 | 8.54 ± 14.39 |
| GRAN(%) | 8.9 ± 4.66 | 9.46 ± 2.33 | 10.8 ± 2.30 | 9.82 ± 3.49 |

RBC: red blood corpuscles; MCV: Mean cell volume of red cells; RDW: Red cell distribution width, HCT: hematocrit; PLT: platelet count; MPV: mean platelet volume; WBC: White blood corpuscle count; HGB: Hemoglobin concentration, LYMF: Lymphocyte; GRAN: granulocyte Clinical Biochemistry Test:

Clinical biochemistry was performed using detection kit purchased from SPINREACT, SA, Spain. The blood left after the hematological studies were allowed to clot for 2 h and serum separated by centrifugation at 3000 rpm for 5 min and subsequently used for clinical biochemistry. Details of the clinical biochemistry (Table 4) and relative organ weight (Table 5) are given below. All the values of different parameters are within the normal range except the marginal rise in the serum bilirubin at the highest dose of compound 1 of formula I. However dose dependency was not observed and therefore the difference is ruled out.

TABLE 4

| Param- | Compound 1 of formula I | | | |
|---|---|---|---|---|
| eters | 47 | 23 | 12 | 0 (vehicle) |
| SGPT (U/L) | 10.8 ± 23 | 12.15 ± 5.50 | 8.42 ± 5.8 | 6.48 ± 2.5 |
| SGOT (U/L) | 3.24 ± 2.91 | 8.64 ± 3.74 | 4.32 ± 1.87 | 8.1 ± 2.29 |
| GammaGT (U/L) | 2.38 ± 0.97 | 2.38 ± 1.19 | 1.78 ± 0.68 | 1.19 ± 0.69 |
| Acid phosphatase | 2.06 ± 1.52 | 2.75 ± 0.74 | 2.98 ± 1.2 | 2.33 ± 0.67 |
| Total protein (mg/dL) | 5.87 ± 0.85 | 5.93 ± 0.41 | 6.44 ± 0.13 | 5.69 ± 0.91 |
| Bilirubin (mg/dL) | 1.41 ± 0.3 | 0.19 ± 0.22 | 0.28 ± 0.30 | 0.19 ± 0.08 |
| Uric acid (mg/dL) | 5.59 ± 2.67 | 7.51 ± 4.13 | 5.89 ± 1.6 | 6.89 ± 2.2 |
| Glucose (mg/dL) | 58 ± 0.07 | 57 ± 0.12 | 49 ± 0.193 | 48 ± 0.14 |

TABLE 5

Percentage Relative organ weights of mice following oral administration of compound 1 of formula I on day 14

| Compound 1 of formula I (mg/kg bw) | Spleen | Liver | Lung | Heart | Kidney |
|---|---|---|---|---|---|
| 47 | 0.55 ± 0.121 | 5.55 ± 0.53 | 0.69 ± 0.17 | 0.46 ± 0.06 | 1.33 ± 0.13 |
| 23 | 0.46 ± 0.06 | 5.83 ± 0.44 | 0.60 ± 0.09 | 0.54 ± 0.09 | 1.43 ± 0.14 |
| 12 | 0.65 ± 0.13 | 5.51 ± 0.30 | 0.72 ± 0.19 | 0.54 ± 0.12 | 1.47 ± 0.33 |
| 0 (Vehicle control) | 0.56 ± 0.22 | 6.51 ± 2.57 | 0.88 ± 0.21 | 0.51 ± 0.03 | 1.64 ± 0.42 |

Necropsy Findings:

At necropsy, no gross or microscopic lesion were found in the vital organs of compound 1 of formula I treated mice, rat and sham controls. Neither there was any accumulation of fluid in the chest and abdomen. All the organs looked normal and similar to sham control groups. In view of this histopathology of the organs have been ruled out.

Immunotoxicity in Mice:

Immunotoxicity in mice was performed in accordance to EPA guideline (1998). No significant changes were observed in the viability of bone marrow cells, splenocyte and lymph node lymphocyte in the compound 1 of formula I treated mice in comparison to sham treated control as judged by trypan blue dye exclusion test. Based on our ELISA results, serum concentrations of total IgG, IgM and IgE in mice treated with compound 1 of formula I were similar to that of sham treated control. Humoral immunity was measured in terms of HA titer and plaque forming cell assay. Results on PFC and HAtitre against SRBC antigen did not show any significant change with single administration of compound 1 of formula I at a dose of 21 mg/kg body weight. Cell mediated immunity was measured in terms of % increase in paw volume in mice sensitized with SRBC. We observed insignificant changes in the DTH response in mice treated with compound 1 of formula I in comparison to sham treated control.

TABLE 6

Immunotoxicity of mice treated with compound 1 of formula I

| Parameters | 47 mg/kg bw | 23 mg/kg bw | 12 mg/kg bw | 0 (Vehicle control) |
|---|---|---|---|---|
| Lymph node lymphocyte viability % (pooled) | >98 | >98 | >98 | >98 |
| Splenocyte viability % | 98.25 ± 0.92 | 97.64 ± 0.73 | 97.69 ± 0.96 | 97.93 ± 0.808 |
| Bone marrow cell viability % | >98 | >98 | >98 | >98 |
| PFC (per $10^6$ lymphocytes) | 2800 ± 1288 | 11633 ± 3636 | 10333 ± 3008 | 7466 ± 1301 |
| HA tire (reciprocal of the last dilution showing positive reaction) | 1280 | 2560 | 2560 | 2560 |
| DTH response (% | 17.75 ± 9.8 | 19.24 ± 10.5 | — | 21.60 ± 6.8 |

In mice, an acute oral of 23 mg/kg was established based on body weight, organ weight, gross necropsy, immunotoxicity, hematology, clinical chemistry and cage side observation.

Example 17

Acute Toxicity Testing of Compound 1 of Formula I

Earlier, LD50 of ICB 14 C6 was derived from in vitro cytotoxicity assay by NRUmethod in 3T3 cells. The predicted acute oral LD50 was found to be 168 mg/kg. In vivo acute oral LD50 was found to be 268 mg/kg bw. For 90d sub-chronic toxicity study the highest dose selected was one-fourth of the limit dose. Four different doses of ICB14 C6 (47, 23, 12 and 0 [vehicle] mg/kg body weight) were prepared in ground nut oil daily for 5 days a week for 90d.

Administration of the Test Substance:

Compound 1 of formula I was administered by oral gavage in water using blunt ended steel canula.

Details of Food and Water Quality:

Pellet food and water treated in a reverse osmosis plant were given to the animals ad libitum.

Inspection of Animals:

On each working day, all mice were inspected and observations recorded. All the mice were weighed weekly.

Blood Samples and Clinical Chemistry:

Blood samples were taken from the retro-orbital sinus on day 91 for hematological and clinical chemistry analyses. Clinical analysis included serum creatinine, serum gammaGT, serum uric acid, serum glucose, serum protein, serum bilirubin, serum GOT/AST and serum GPT/ALT. Hematology including white blood cell count was analyzed with the help of Automatic Hematology Analyzer (Medonic).

Histopathology:

After 90d of oral treatment with ICB3001, 3 mice in each group were sacrificed and major organs were placed in 10% formalin to prepare histological slides. The slides were stained by haematoxylin-eosin dye.

Statistics:

In all results, the mean±sd is given if not specified otherwise, the Students t test was used to calculate statistical significance.

Cage Side Observations:

From the day of administering the drug, 30 min cage side observation of the animals were performed every day (5 days a week) till the day of sacrifice. No signs and symptoms of restlessness, perinasal wetness and rapid rate of respiration were observed post administration. All the animals appeared normal. No signs of staggering locomotion, sluggish behavior or nasal discharge were observed at any time point. However on 10 week a mouse of 47 mg/kg dose group appeared in a moribund state and on the 11$^{th}$ weekend it died. On the 12$^{th}$ week we found the mouse in a shrunken state as it was kept in the deep freezer. The conditions of the vital organs were also found shrunken and hence no histopathology was performed.

Feed and water consumption in compound 1 of formula I treated mice were comparable to sham controls as judged from the leftover feed and water level in the bottles.

Gross physical examinations did not reveal any signs of diagnostic clinical importance. There was no noticeable behavioral change in any of the treated groups of mice.

TABLE 7

Body weight of mice treated with compound 1 of formula I

| Week | 47 mg/kg bw | 23 mg/kg bw | 12 mg/kg bw | 0 mg/kg bw |
|---|---|---|---|---|
| 0 | 31.02 ± 3.18 | 30.24 ± 2.19 | 31.13 ± 4.18 | 30.5 ± 3.62 |
| 1 | 26.63 ± 3.06 | 26.53 ± 1.31 | 28.33 ± 1.07 | 30.06 ± 2.77 |
| 2 | 28.7 ± 3.9 | 29.16 ± 1.3 | 29.36 ± 1.01 | 30.9 ± 3.6 |
| 3 | 30.33 ± 4.5 | 28.83 ± 1.00 | 28.5 ± 0.43 | 31.23 ± 3.94 |
| 4 | 30.33 ± 3.67 | 28.56 ± 2.93 | 27.93 ± 0.28 | 31.43 ± 3.85 |
| 5 | 31.23 ± 3.21 | 27.2 ± 3.37 | 28.46 ± 0.83 | 31.86 ± 2.54 |
| 6 | 29.76 ± 4.21 | 29.46 ± 1.84 | 29.6 ± 0.92 | 28.03 ± 4.06 |
| 7 | 30.36 ± 4.45 | 30.46 ± 1.84 | 30.36 ± 0.83 | 30.33 ± 2.99 |
| 8 | 29.3 ± 3.55 | 29.8 ± 0.91 | 30.83 ± 1.25 | 29.6 ± 2.46 |
| 9 | 29.56 ± 4.52 | 30.06 ± 1.36 | 30.56 ± 1.62 | 30.33 ± 3.25 |
| 10 | 29.46 ± 5.68 | 29.96 ± 1.89 | 28.83 ± 0.70 | 29.66 ± 3.37 |
| 11 | 30.4 ± 7.63 | 28.13 ± 1.25 | 31.46 ± 0.72 | 32.26 ± 3.71 |
| 12 | 30.15 ± 2.14 | 27.73 ± 1.18 | 31.2 ± 0.75 | 32.46 ± 2.82 |
| 13 | 29.3 ± 2.7 | 27.9 ± 0.96 | 30.8 ± 1.4 | 32.3 ± 3.6 |

After 90 days of administration of compound 1 of formula I to mice, no dose related differences in body weight gain were found.

Relative Organ Weight Data:

TABLE 8

Percentage Relative organ weights of mice following oral administration of compound 1 of formula I for 90 days

| Groups | Spleen | Liver | Lung | Heart | Kidney |
|---|---|---|---|---|---|
| 47 mg/kg bw | 0.64 ± 0.08 | 4.90 ± 0.63 | 0.57 ± 0.021 | 0.51 ± 0.87 | 1.30 ± 0.12 |
| 23 mg/kg bw | 0.43 ± 0.01 | 4.59 ± 0.72 | 0.56 ± 0.06 | 0.50 ± 0.07 | 1.56 ± 0.12 |
| 12 mg/kg bw | 0.46 ± 0.03 | 4.89 ± 0.03 | 0.631 ± 0.04 | 0.46 ± 0.05 | 1.44 ± 0.056 |
| 0 mg/kg bw | 1.37 ± 0.38 | 4.23 ± 0.67 | 0.74 ± 0.08 | 0.42 ± 0.11 | 1.16 ± 0.19 |

Percentage relative organ weights did not demonstrate dose dependant changes. However, the relative weight of liver in compound 1 of formula I treated mice is marginally higher in comparison to sham treated control mice (0 mg/kg body weight)

Hematology:

Before sacrifice, blood was drawn from the retro-orbital sinus of mice with the help of heparinised capillary tubes and hematological parameters were assessed with the help of Automatic Hematology Analyzer (Medonic CA535). Detailed hematology is presented in Table 9.

TABLE 9

Hematological tests with relevant base line values in mice treated with compound 1 of formula I with different doses

| Parameters | 47 mg/kg bw | 23 mg/kg bw | 12 mg/kg b.w | 0 mg/kg bw |
|---|---|---|---|---|
| RBC (×10$^6$/mm$^3$) | 8.51 ± 0.323 | 9.82 ± 0.014 | 10.07 ± 0.67 | 9.49 ± 0.62 |
| PLT (×10$^3$/mm$^3$) | 319 ± 120 | 306 ± 106 | 272 ± 93 | 323 ± 110 |
| WBC (×10$^3$/mm$^3$) | 10.16 ± 1.03 | 10.85 ± 2.11 | 8.66 ± 1.27 | 10.8 ± 1.52 |
| HGB (g/dL) | 12.13 ± 0.57 | 13.85 ± 0.35 | 13.76 ± 0.55 | 10.4 ± 0.76 |

*Significant ($p < 0.05$);
** significant ($p < 0.001$) RBC: red blood corpuscles (7-10 × 10$^6$/mm$^3$);
PLT: platelet count (400-700 × 10$^3$/mm$^3$); WBC: White blood corpuscle count (9-18 × 10$^3$/mm$^3$); HGB: Hemoglobin concentration (10-14).

In all the groups, the platelet counts were below the normal range. However, in comparison to sham control group the differences were statistically insignificant. Hemoglobin, RBC and WBC counts in all the groups were found within the normal range.

Clinical Biochemistry Test:

The blood left after the hematological studies were allowed to clot for 2 h and serum separated by centrifugation at 3000 rpm for 5 min and subsequently used for clinical biochemistry using kits from Spinreact S.A. (Girona, Spain). Procedural details given in the technical bulletin were followed for the measurement of different serum parameters. Clinical biochemistry results are presented in Table 10.

TABLE 10

Clinical biochemistry of compound 1 of formula I treated
mice for 90 days in comparison to respective sham control

| Parameters (normal value) | 47 mg/kg bw | 23 mg/kg bw | 12 mg/kg bw | 0 mg/kg bw |
|---|---|---|---|---|
| LDH (120-240 U/L) | 210.5 ± 25 | 198.6 ± 27 | 175.3 ± 18 | 183.8 ± 30 |
| Creatinine (0.64-1.0 mg/dL) | 1.36 ± 0.56 | 1.10 ± 0.65 | 1.03 ± 0.48 | 0.87 ± 0.30 |
| gammaGT (4-18 U/L) | 15.66 ± 2.63 | 15.29 ± 5.38 | 12.73 ± 6.74 | 8.49 ± 3.89 |
| Total protein (6.7-8.7 g/dL) | 7.78 ± 1.37 | 6.52 ± 2.61 | 8.63 ± 1.81 | 7.52 ± 0.55 |
| Bilirubin (1.1 mg/dL) | 0.54 ± 0.39 | 0.37 ± 012 | 0.91 ± 0.47 | 1.04 ± 0.78 |
| Uric acid (3.4-7.0 mg/dL) | 5.59 ± 1.26 | 7.15 ± 0.62 | 6.05 ± 3.9 | 6.90 ± 2.4 |
| Glucose (55-110 mg/dL) | 86.42 ± 6.39 | 61.66 ± 13.08 | 79.89 ± 22.82 | 98.33 ± 11.39 |
| GOT/AST (<19 U/L @ 25° C.) | 5.30 ± 1.55 | 13.56 ± 6.88 | 12.25 ± 2.18 | 10.17 ± 2.69 |
| GPT/ALT (<22 U/L @ 25° C.) | 5.71 ± 9.89 | 12.84 ± 7.9 | 8.56 ± 3.79 | 4.82 ± 2.04 |

Total protein, bilirubin, glucose and serum uric acid levels were found within the normal ranges in all the groups. Creatinine levels at a dose of 47 mg/kg compound 1 of formula I was marginally above the normal range and sham control. Activities of AST, ALT and gammaGT enzymes were also found within the normal range in all the doses of compound 1 of formula I treated mice.

Necropsy Findings:

At necropsy after 90d of compound 1 of formula I exposure no gross or microscopic lesion were found in the vital organs of compound 1 of formula I treated mice and controls. Neither there was any accumulation of fluid in the chest and abdomen. All the organs looked normal and similar to sham control groups.

Figure 7:
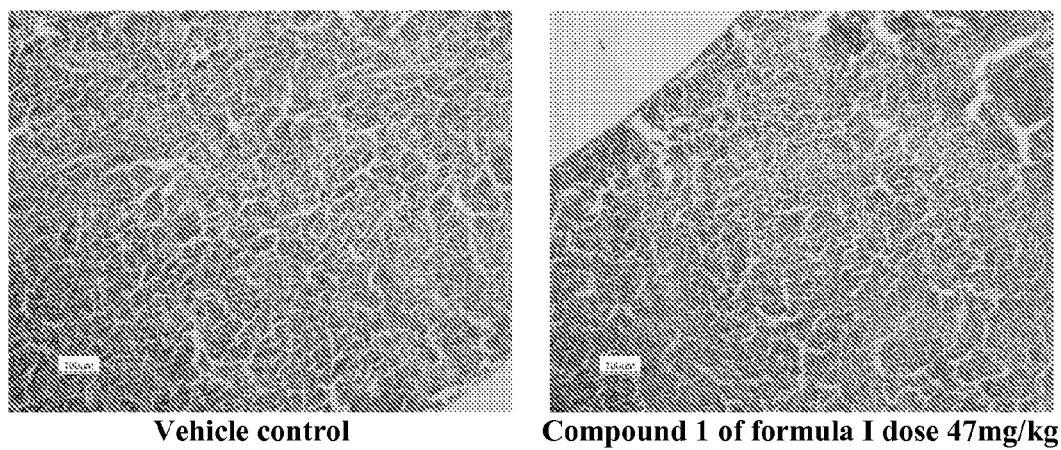
Figure 8:
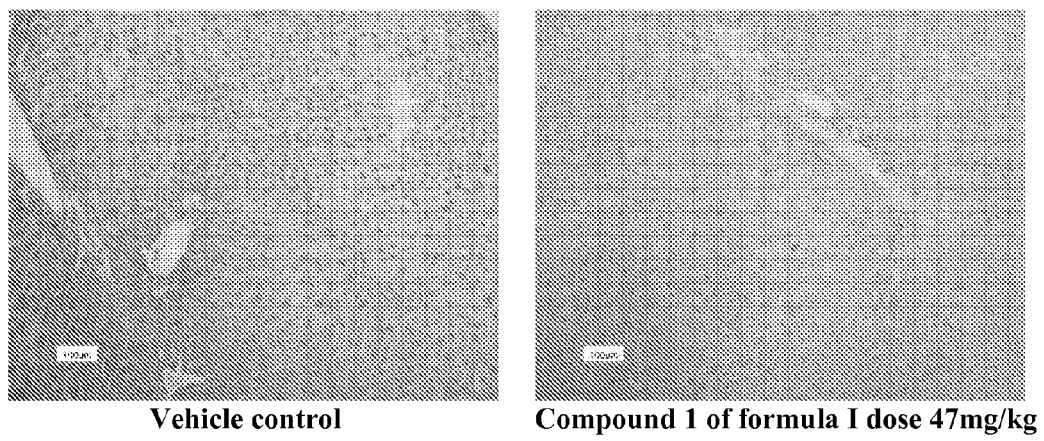

Histopathology:

Histological features of spleen from sham control mice showed normal histoarchitecture with germinal centre, red pulp and marginal zone of white pulp. Similar features were apparent in spleen sections of 47 mg/kg of compound 1 of formula I treated mice in all the doses (FIG. 7). Liver sections from sham treated control mice revealed the presence of polygonal hepatic cells. Few binucleated hepatic cells were also visible in the treated group. Kuffer cells on to the sinusoidal wall were not observed. In liver section of 47 mg/kg bw treated mice, a few hypertrophied hepatocytes were observed. Kuffer cells were not visible. Mild necrosis of the hepatocytes were seen in the liver of mice treated with 47 mg/kg of compound 1 of formula I. At other doses no change in the structure of hepatic cells were observed (FIG. 8).

Figure 9:
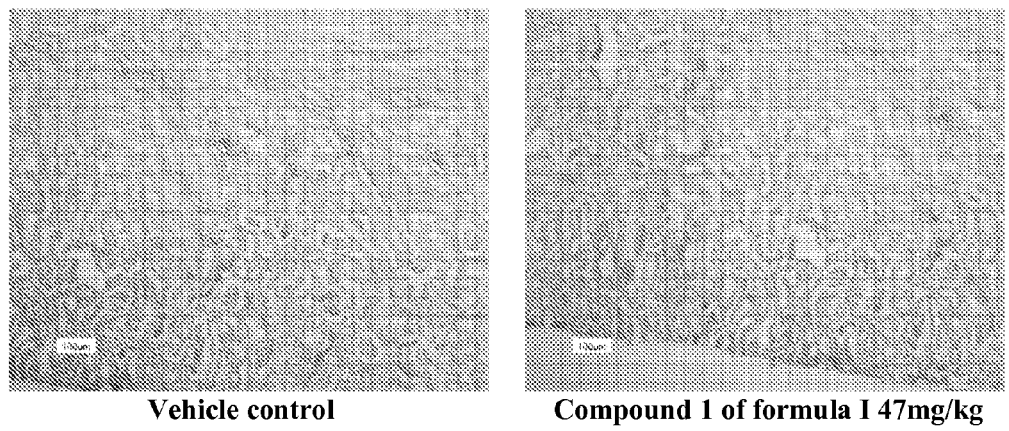

The corticular region of the sham treated kidney showed enormous number of Bowman's capsules that were uniformly distributed throughout the corticular region. Majority of the capsules were oval and round in shape but few elliptical shaped Bowman's capsules were also encountered. In the kidney of compound 1 of formula I treated mice no significant changes were observed (FIG. 9).

Figure 10:
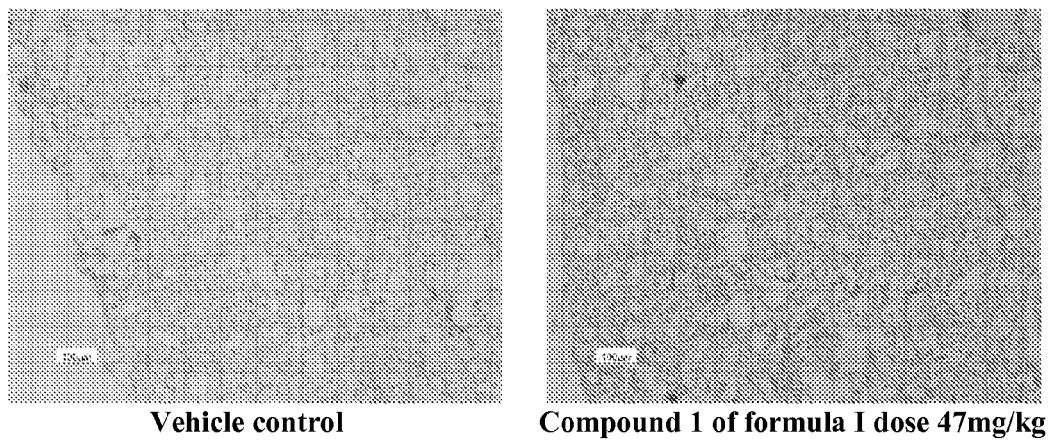
Figure 11:
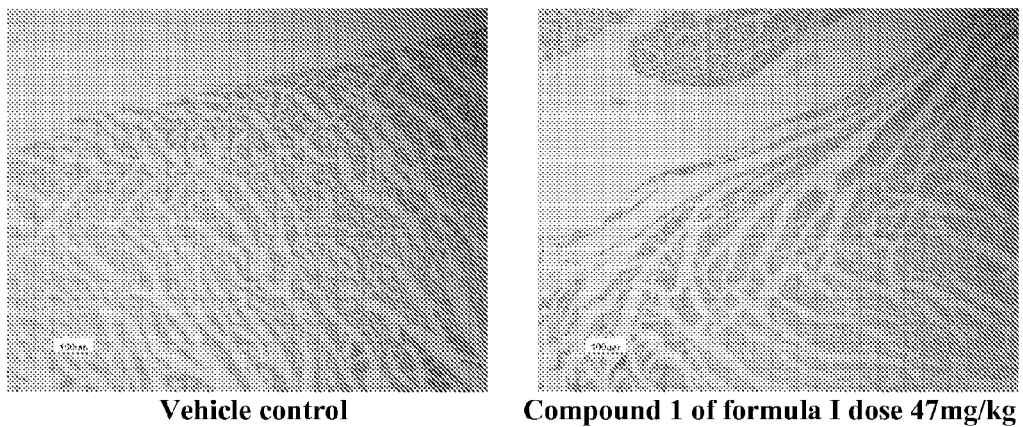
Figure 12A:
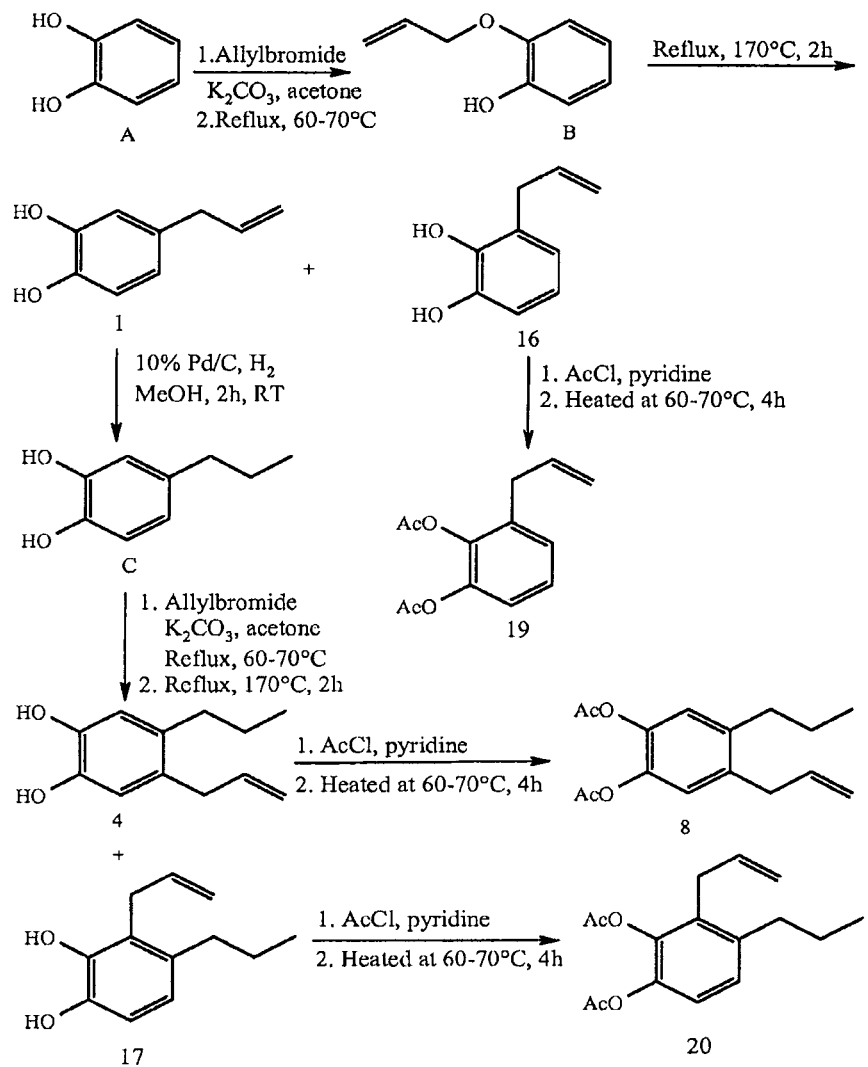
Figure 12B:
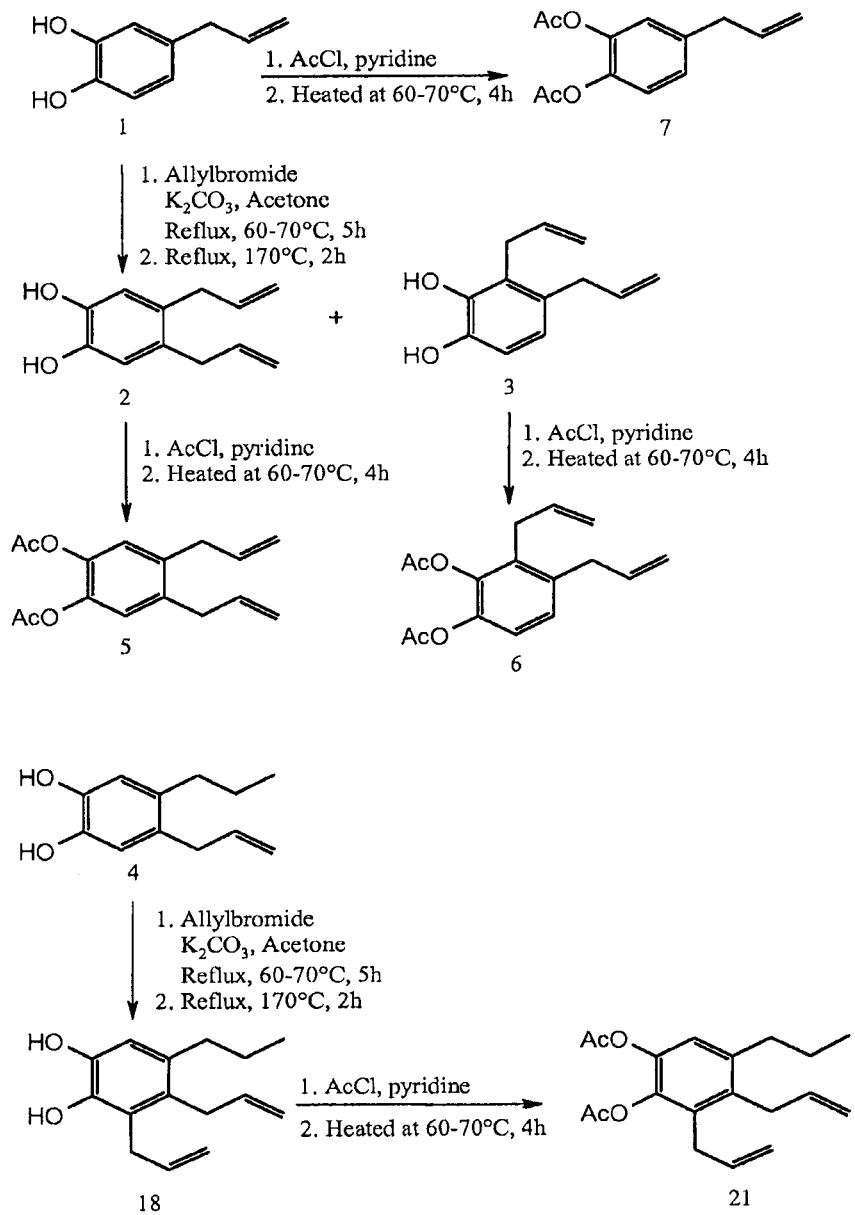
Figure 12C:
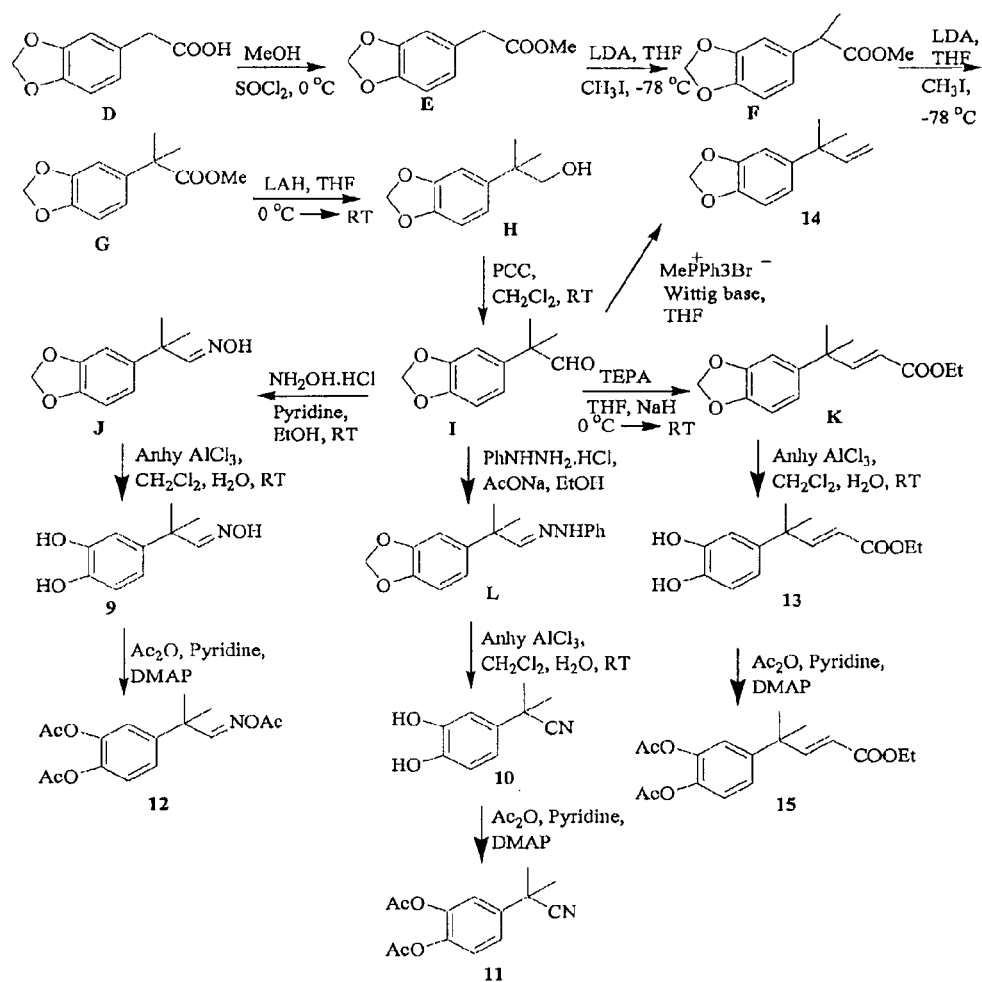

The lungs of sham treated mice showed normal cellular architecture with thin intercellular septum. Mouse treated with compound 1 of formula I at a dose of 47 mg/kg showed fair distribution of alveoli with slight thickening of intercellular septum and migration of polymorphonuclear lymphocytes (FIG. 10). In the heart sections no significant changes in the histo-architecture was observed between the vehicle control and compound 1 of formula I treated mice FIG. 11).

Immunotoxicity in Mice:

TABLE 11

Immunotoxicity of mice treated with Vehicle control compound 1 of formula I

| Parameters | 47 mg/kg bw | 23 mg/kg bw | 12 mg/kg bw | 0 mg/kg bw |
|---|---|---|---|---|
| Lymph node lymphocyte viability % (pooled) | 98.17 ± 0.05 | 98.28 ± 0.80 | 97.40 ± 0.61 | 98.48 ± 0.47 |
| Splenocyte viability % | 96.45 ± 0.62 | 96.56 ± 0.80 | 96.79 ± 0.36 | 94.17 ± 5.22 |
| Bone marrow cell viability % | 95.45 ± 0.31 | 96.80 ± 1.15 | 97.26 ± 0.88 | 96.56 ± 0.22 |
| Total IgG (mg/mL) | 6.11 ± 0.25** | 15.21 ± 0.31 | 12.98 ± 0.53 | 13.19 ± 3.05 |
| Total IgM | 1.02 ± 0.30 | 0.57 ± 0.17 | 6.65 ± 0.13 | 0.54 ± 0.16 |
| Total IgA (ng/mL) | 167 ± 2.12 | 207.25 ± 9.7 | 264.25 ± 28.6 | 209 |
| Total IgE | 0.65 ± 0.09 | 0.74 ± 0.23 | 0.69 ± 0.115 | 0.83 |
| PFC (per $10^6$ lymphocytes) | 1849 ± 780** | 4911 ± 873 | 5533 ± 437 | 7231 ± 1771 |
| HA tire (reciprocal of the last dilution showing positive reaction) | 320 | 640 | 1280 | 1280 |
| DTH response (% increase in paw volume) | 11.28 ± 3.69 | 11.55 ± 3.77 | 12.12 ± 2.96 | 17.44 ± 3.28 |

**Significant (p < 0.001)

Lymph node lymphocyte, splenocytes and bone marrow cell viabilities were found >94% in all the groups of compound 1 of formula I treated mice. Sharp decrease in total IgG level was observed in mice treated at a dose of 47 mg/kg. IgE level remained unaffected. Dose dependant decrease in B cell function was observed. HA titre followed a similar pattern as the PFC response. Cell mediated immune response in terms of % increase in paw volume also followed a dose dependent increase in mice. However, changes were insignificant in comparison to sham control.

Advantages of the Invention
  Present invention provides compounds for the treatment of bronchial asthma.
  Bronchial asthma may be treated by the inhibition of IL-4 or IL-5 pathway.
  Asthma can be treated by administering the compound of general formula 1 through oral, intranasal, route or by inhalation to a mammal in need thereof.
  Compound of general formula 1 may be used for reducing perivascular and peribronchial inflammation

The invention claimed is:

1. A method for the treatment of a mammal suffering from bronchial asthma consisting essentially of administering to the mammal in need thereof a therapeutically effective amount of:
  i. one or more compounds general formula 1 having the structure:

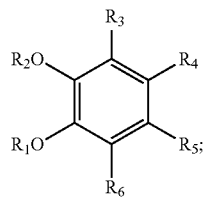

wherein $R_1$=—H or —COCH$_3$, $R_2$=—H or —COCH$_3$, or wherein $R_1$ and $R_2$ are covalently coupled to —CH$_2$— comprising a five member ring with the structure:

wherein $R_4$=—H or —CH$_2$—CH=CH$_2$ or —CH$_2$— CH$_2$—CH$_3$
  wherein $R_5$=—H or —CH$_2$—CH=CH$_2$; and
  wherein $R_6$=—H or —CH$_2$—CH=CH$_2$;
  ii. one or more compounds with formula I having the structure:

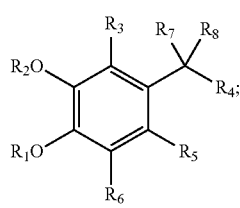

wherein $R_1$=—H or —COCH$_3$, $R_2$=—H or —COCH$_3$, or wherein $R_1$ and $R_2$ are covalently coupled to —CH$_2$— comprising a five member ring with the structure:

wherein $R_3$=—H;
  wherein $R_4$=—CH=CH$_2$ or —CH$_2$—CH$_3$ or —CH=NOH or —CN or —CH=NOAc or —CH=CH—COOEt;
  wherein $R_5$=—H or —CH$_2$—CH=CH$_2$;
  wherein $R_6$=—H or —CH$_2$—CH=CH$_2$
  wherein $R_7$=—H or —CH$_3$; and
  wherein $R_8$=—H or —CH$_3$;
  iii. one or more compounds with formula II having the structure:

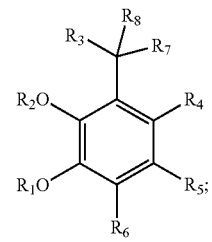

wherein $R_1$=—H or —COCH$_3$, $R_2$=—H or —COCH$_3$, or wherein $R_1$ and $R_2$ are covalently coupled to —CH$_2$— comprising a five member ring with the structure:

wherein $R_3$=—CH=CH$_2$
  wherein $R_4$=—H or —CH$_2$—CH=CH$_2$ or —CH$_2$— CH$_2$—CH$_3$;
  wherein $R_5$=—H or —CH$_2$—CH=CH$_2$;
  wherein $R_6$=—H or —CH$_2$—CH=CH$_2$;
  wherein $R_7$=—H; and
  wherein $R_8$=—H; and
wherein the bronchial asthma is treated by IL-4 or IL-5 pathway inhibition.

2. The method of claim 1, wherein said one or more compounds comprises:
  (1) 4-allyl-benzene-1,2-diol (hydroxychavicol),
  (2) 4,5-diallylbenzene-1,2-diol,
  (3) 3,4-diallylbenzene-1,2-diol,
  (4) 4-allyl-5-propylbenzene-1,2-diol,
  (5) 4,5-diallyl-1,2-phenylene diacetate,
  (6) 3,4-diallyl-1,2-phenylene diacetate,
  (7) 4-allyl-1,2-phenylene diacetate,
  (8) 4-allyl-5-propyl-1,2-phenylene diacetate,
  (9) 2-(3,4-dihydroxyphenyl)-2-methylpropanal oxime,
  (10) 2-(3,4-dihydroxyphenyl)-2-methylpropanenitrile,
  (11) 4-(2-cyanopropan-2-yl)-1,2-phenylene diacetate,

(12) 4-(1-(acetoxyimino)-2-methylpropan-2-yl)-1,2-phenylene diacetate,
(13) (E)-ethyl 4-(3,4-dihydroxyphenyl)-4-methylpent-2-enoate,
(14) 5-(2-methylbut-3-en-2-yl)benzo[d][1,3]dioxole,
(15) (E)-4-(5-ethoxy-2-methyl-5-oxopent-3-en-2-yl)-1,2-phenylene diacetate,
(16) 3-allyl-benzene-1,2-diol,
(17) 3-allyl-4-propylbenzene-1,2-diol,
(18) 3,4-diallyl-5-propylbenzene-1,2-diol,
(19) 3-allyl-1,2-phenylene diacetate,
(20) 3-allyl-4-propyl-1,2-phenylene diacetate; or
(21) 3,4-diallyl-5-propyl-1,2-phenylene diacetate.

3. The method of claim 1, wherein the compound is administered through oral, intranasal, route or by inhalation to said mammal.

4. The method of claim 1, wherein said compound increases $PC_{200}$ Mch in the range of 0.1 mg to 10.0 mg per kg body weight.

5. The method of claim 1, wherein the concentration of the compound used for Inhibition of stimulation-induced IL-4 ($IC_{50}$) is in the range of 5 to 30 μM.

6. The method of claim 1, wherein the concentration of the compound used for Inhibition of stimulation-induced IL-5 ($IC_{50}$) is in the range of 4.5 to 35 μM.

7. The method of claim 1, wherein the concentration of the compound used for reducing immunoglobulin E (IgE) is in the range of 0.1 mg to 10.0 mg per kg body weight.

8. The method of claim 1, wherein the concentration of the compound used for reducing lung inflammation is in the range of 5.0 mg to 10.0 mg per kg body weight.

9. The method of claim 1, wherein the concentration of the compound used for reducing perivascular and peribronchial inflammation is in the range of 5.0 mg to 10.0 mg per kg body weight.

10. The method of claim 3, wherein said compound is administered orally.

11. The method of claim 3, wherein said oral administration comprises capsule, syrup, powder or granules.

12. The method of claim 1, wherein said compound of is administered at a dosage level between 0.1 mg to 10.0 mg per kg body weight twice a day for 6 months.

* * * * *